(12) United States Patent
Goodby et al.

(10) Patent No.: US 7,351,452 B2
(45) Date of Patent: Apr. 1, 2008

(54) LIQUID CRYSTALLINE COMPOUNDS CONTAINING A BIPHENYL CORE

(75) Inventors: John W Goodby, Hull (GB); Michael Hird, Hull (GB); Kenneth J Toyne, Hull (GB); Chu C Dong, Hull (GB); Robert D. C Richards, Hull (GB)

(73) Assignee: Qinetiq Limited, London (GB)

( * ) Notice: Subject to any disclaimer, the term of this patent is extended or adjusted under 35 U.S.C. 154(b) by 355 days.

(21) Appl. No.: 10/493,534

(22) PCT Filed: Nov. 7, 2002

(86) PCT No.: PCT/GB02/05045

§ 371 (c)(1),
(2), (4) Date: Apr. 22, 2004

(87) PCT Pub. No.: WO03/040074

PCT Pub. Date: May 15, 2003

(65) Prior Publication Data

US 2005/0001200 A1    Jan. 6, 2005

(30) Foreign Application Priority Data

Nov. 8, 2001    (GB)    .................... 0126844.0

(51) Int. Cl.
C09K 19/30    (2006.01)
C09K 19/34    (2006.01)
C09K 19/12    (2006.01)
C07C 25/13    (2006.01)
C07C 43/225    (2006.01)
C07D 319/06    (2006.01)
C07F 7/08    (2006.01)

(52) U.S. Cl. ............. 428/1.1; 252/299.61; 252/299.63; 252/299.66; 556/454; 568/647; 570/129; 570/130; 570/131; 570/162; 549/369

(58) Field of Classification Search .................. 428/1.1, 428/299.61, 299.63, 299.66, 299.67; 252/299.61, 252/299.63, 299.66; 570/129, 130, 131, 570/162; 549/369; 568/647; 556/454

See application file for complete search history.

(56) References Cited

U.S. PATENT DOCUMENTS

| | | | |
|---|---|---|---|
| 4,886,619 A | 12/1989 | Janulis | |
| 5,254,747 A | 10/1993 | Janulis | |
| 5,399,701 A | 3/1995 | Janulis | |
| 5,626,793 A | 5/1997 | Reiffenrath et al. | |
| 5,837,162 A | 11/1998 | Reiffenrath et al. | |
| 6,159,393 A | 12/2000 | Tarumi et al. | |
| 6,759,101 B2* | 7/2004 | Gough et al. | 428/1.1 |
| 6,783,812 B2* | 8/2004 | Wand et al. | 428/1.1 |
| 6,838,128 B1* | 1/2005 | Wand et al. | 428/1.1 |
| 7,083,832 B2* | 8/2006 | Wand et al. | 428/1.1 |

(Continued)

FOREIGN PATENT DOCUMENTS

DE    42 15 277 A    11/1993

(Continued)

OTHER PUBLICATIONS

English translation by computer for JP 06-264058, http://www4.ipdl.ncipi.jp/Tokujitu/PAJdetail.ipdl?N0000=60&N0120=01&N2001=2&N3001=H06-264058.*

(Continued)

Primary Examiner—Shean C Wu
(74) Attorney, Agent, or Firm—Nixon & Vanderhye P.C.

(57) ABSTRACT

A compound of formula (I)

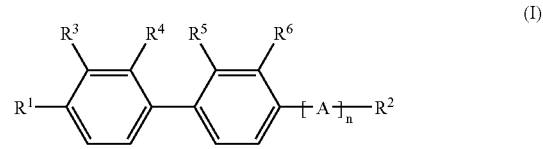

or a dimer thereof; where $R^1$ and $R^2$ are independently selected from optionally substituted alkyl, optionally substitituted alkenyl, optionally substituted alkynyl, a functional group or a group of sub-formula (i)

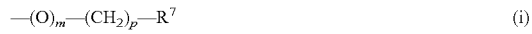

where m is 0 or 1; p is an integer of from 1 to 12; $R^7$ is a group of formula $-C_qX_{2q+1}$ where q is an integer of from 1 to 12 and X is halogen such as fluoro, or $R^7$ a group of sub-formula (ii)

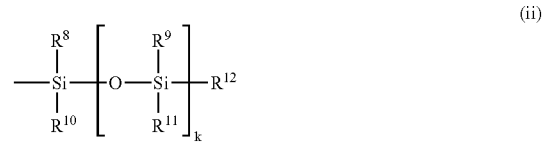

where k is an integer of from 1 to 10, $R^8$, $R^{10}$, and $R^{12}$ and each $R^9$ and $R^{11}$ are independently selected from alkyl, alkenyl or aryl, such as lower alkyl and in particular methyl; provided that at least one of $R^1$ or $R^2$ is a group of sub-formula (i);
$R^3$, $R^4$, $R^5$ and $R^6$ are independently selected from hydrogen or halogen, and in particular fluorine, n is 0 or 1, and A is a ring structure as specified. Compounds of formula (I) may have liquid crystal properties and/or be useful in liquid crystal devices.

26 Claims, No Drawings

U.S. PATENT DOCUMENTS

| | | | |
|---|---|---|---|
| 7,183,447 B2* | 2/2007 | Pauluth et al. | 570/129 |
| 7,195,719 B1* | 3/2007 | Wand et al. | 252/299.61 |
| 2003/0017278 A1* | 1/2003 | Wand et al. | 428/1.1 |

FOREIGN PATENT DOCUMENTS

| | | |
|---|---|---|
| DE | 42 22 371 A | 1/1994 |
| DE | 44 27 199 A | 2/1996 |
| EP | 0 255 236 A | 2/1988 |
| EP | 0554109 A1 | 8/1993 |
| EP | 0704744 A1 | 4/1996 |
| GB | 2 339 778 A | 2/2000 |
| GB | 2 348 883 A | 10/2000 |
| JP | 06-264058 * | 9/1994 |
| JP | 09-052852 A | 2/1997 |
| JP | 11 246451 A | 9/1999 |
| WO | WO 89/02425 A1 | 3/1989 |
| WO | 90/01021 A | 2/1990 |
| WO | 92/13928 A | 8/1992 |
| WO | 96/05159 A | 2/1996 |
| WO | 00/39062 A | 7/2000 |

OTHER PUBLICATIONS

CAPLUS 2002: 172022.*

De Givenchy et al; "Synthesis and Mesomorphic Behavior of Chiral Partially Fluorinated Liquid Crystal Incorporating S-2-Methylbutyl"; Molecular Crystals and Liquid Crystals Science and Technology, Section A: Molecular Crystals and Liquid Crystals, 1999, vol. 332, pp. 2519-2526, XP008013802.

Kawakami et al; "Synthesis and Characterization of Liquid Crystalline Polystyrenes With Disiloxane Linkage in the Spacer"; Polymer Bulletin, Springer Verlag. Heidelberg, DE, vol. 36, No. 6, Jun. 1, 1996, pp. 653-658, XP000588744.

Skelton et al; "Aromatic Liquid Crystals With a Trifluoromethyl Group in the Terminal Chain for use in Nematic Mixtures"; Liquid Crystals, Taylor and Francis LTD, London, GB, vol. 28, No. 5, May 2001, pp. 749-759, XP001124194.

Kelly et al; "Nematic Liquid Crystals With a Trifluoromthyl Group"; Molecular Crystals and Liquid Crystals Science and Technology, Section A: Molecular Crystals and Liquid Crystals, 2001, vol. 364, pp. 873-880x XP008013786.

* cited by examiner

LIQUID CRYSTALLINE COMPOUNDS CONTAINING A BIPHENYL CORE

The present invention relates to novel compounds, which may be useful in liquid crystal devices, for example because they have the properties of liquid crystals, together with processes for their preparation and liquid crystal devices incorporating them.

The term "liquid crystals" is well known. It refers to compounds which, as a result of their structure, will align themselves in a similar orientation, preferably at working temperatures, for example of from −40 to 200° C. These materials are useful in various devices, in particular the liquid crystal display devices or LCDs.

Liquid crystals can exist in various phases. In essence there are three different classes of liquid crystalline material, each possessing a characteristic molecular arrangement. These classes are nematic, chiral nematic (cholesteric) and smectic.

Broadly speaking, the molecules of nematic compounds will align themselves in a particular orientation in a bulk material. Smectic materials, in addition to being orientated in a similar way, will align themselves closely in layers.

A wide range of smectic phases exists, for example smectic A and smectic C. In the former, the molecules are aligned perpendicularly to a base or support, whilst in the latter, molecules may be inclined to the support. Some liquid crystal materials possess a number of liquid crystal phases on varying the temperature. Others have just one phase. For example, a liquid crystal material may show the following phases on being cooled from the isotropic phase:—isotropic—nematic—smectic A—smectic C—solid. If a material is described as being smectic A then it means that the metal possesses a smectic A phase over a useful working temperature range.

Such materials are useful, in particular in display devices where their ability to align themselves and to change their alignment under the influence of voltage, is used to impact on the path of polarised light, thus giving rise to liquid crystal displays. These are widely used in devices such as watches, calculators, display boards or hoardings, computer screens, in particular laptop computer screens etc. The properties of the compounds which impact on the speed with which the compounds respond to voltage charges include molecule size, viscosity ($\Delta n$), dipole moments ($\Delta \epsilon$), conductivity etc.

U.S. Pat. Nos. 5,547,604, 5,855,813, 5,942,155 and Japanese Patent Publication Nos. 01144491, 01268785 and 02180890 describe a range of liquid crystal compounds.

The applicants have found a new class of chemicals many of which have useful liquid crystal properties.

According to the present invention there is provided a compound of formula (I)

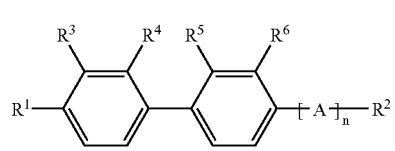

(I)

or a dimer thereof;
where $R^1$ and $R^2$ are independently selected from optionally substituted alkyl, optionally substituted alkenyl, optionally substituted alkynyl, a functional group or a group of sub-formula (i)

(i)

where m is 0 or 1;
p is an integer of from 1 to 12;
$R^7$ is a group of formula $-C_qX_{2q+1}$ where q is an integer of from 1 to 12 and X is halogen such as fluoro,
or $R^7$ is a group of sub-formula (ii)

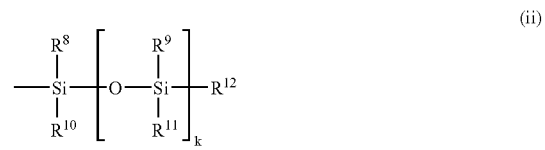

(ii)

where k is an integer of from 1 to 10, $R^8$, $R^{10}$, and $R^{12}$ and each $R^9$ and $R^{11}$ are independently selected from alkyl, alkenyl or aryl, such as lower alkyl and in particular methyl;
provided that at least one of $R^1$ or $R^2$ is a group of sub-formula (i);
$R^3$, $R^4$, $R^5$ and $R^6$ are independently selected from hydrogen or halogen, and in particular fluorine,
n is 0 or 1, and A is a group of sub-formula (iii), (iv), (v), (vi) or (vii)

(iii)

(iv)

(v)

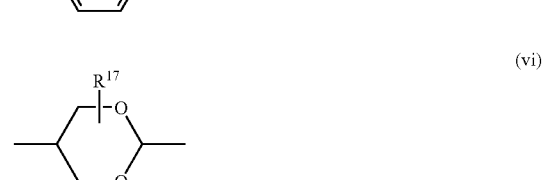

(vi)

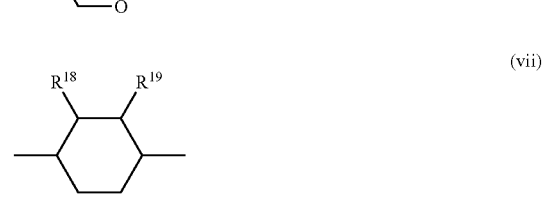

(vii)

where $R^{13}$, $R^{14}$, $R^{15}$, $R^{16}$, $R^{17}$, $R^{18}$ and $R^{19}$ are independently selected from hydrogen or halo, such as fluoro, and the group A may be orientated in either direction, so that the group $R^2$ is attached at either of the available bonds in sub-formula (iii)-(vii).

Preferably compounds of formula (I) are selected because they have useful liquid crystal properties as described in more detail below. However, others may be useful as dopants, in particular chiral dopants in liquid crystal mixtures.

Dimers of compounds of formula (I) are suitably prepared by condensation of the groups $R^7$, for example by formation of a siloxane chain from two groups of sub-formula (ii).

As used herein the term "hydrocarbyl" refers to organic groups comprising carbon and hydrogen atoms such as alkyl, alkenyl, alkynyl, cycloalkyl, aryl or aralkyl. The term "alkyl" refers to straight or branched chain alkyl group, suitably containing up to 20, more suitably up to 10 and preferably up to 6 carbon atoms. The expression "lower" used in relation to alkyl groups for instance, indicates an upper limit of 6 carbon atoms, and suitably is $C_{1-3}$. The term "alkenyl" or "alkynyl" refers to optionally. The term "alkylene" refers to such groups which are divalent and "cycloalkyl" refers to such groups which have at least 3 carbon atoms, and which are cyclic in structure. The term "aryl" refers to aromatic rings such as phenyl and naphthyl. The term aralkyl refers to alkyl groups substituted by aryl groups such as benzyl.

References to "heterocyclic groups" refer to rings which may be mono or bi-cyclic and aromatic, non-aromatic or, in the case of bicyclic rings, partially aromatic and partially non-aromatic. These rings suitably contain from 3 to 20 atoms, up to seven of which are heteroatoms selected from oxygen, nitrogen or sulphur.

The term "functional group" as used herein refers to reactive groups such as halo, cyano, nitro, oxo, —OC(O)$R^a$, —O$R^a$, —C(O)O$R^a$, S(O)$_t R^a$, N$R^b R^c$, OC(O)N$R^b R^c$, C(O)N$R^b R^c$, OC(O)N$R^b R^c$, —N$R^c$C(O)$_n R^b$, —N$R^a$CON$R^b R^c$, —C═NO$R^a$, —N═C$R^b R^c$, S(O)$_t$ N$R^b R^c$, C(S)$_n R^a$, C(S)O$R^a$, C(S)N$R^b R^c$ or —N$R^b$S(O)$_t R^a$ where $R^a$, $R^b$ and $R^c$ are independently selected from hydrogen or optionally substituted hydrocarbyl, or $R^b$ and $R^c$ together form an optionally substituted ring which optionally contains further heteroatoms such as S(O)$_s$, oxygen and nitrogen, n' is an integer of 1 or 2, s is 0, 1 or 2, t is 0 or an integer of 1-3. In particular the functional groups are groups such as halo, cyano, nitro, OXO, C(O)$_n R^a$, O$R^a$, S(O)$_t R^a$, N$R^b R^c$, OC(O)N$R^b R^c$, C(O)N$R^b R^c$, OC(O)N$R^b R^c$, —N$R^c$C(O)$_n R^b$, —N$R^a$CON$R^b R^c$, —N$R^a$CSN$R^b R^c$, —C═NO$R^a$, —N═C$R^b R^c$, S(O)$_t$N$R^b R^c$, or —N$R^b$S(O)$_t R^a$ where $R^a$, $R^b$ and $R^c$, n' and t are as defined above.

Suitable optional substituents for hydrocarbyl groups $R^a$, $R^b$ and $R^c$ are halo, cyano, nitro, oxo, carboxy or alkyl esters thereof, alkoxy, alkoxycarbonyl, amido, mono or di-alkylamido, amino, mono or di-alkylamino, alkyl sulphonyl, or thioalkyl.

Particular examples of functional groups for $R^1$ and $R^2$ are cyano, halo such as fluoro, or most preferably, a group of formula O$R^a$ where $R^a$ is as defined above. A particularly preferred example of a group $R^a$ in this instance is alkyl.

Alternative functional groups for $R^1$ and $R^2$ are groups of formula OC(O)$R^a$, —C(O)O$R^a$ where $R^a$ is preferably a branched alkyl group which suitably carries a halo substituent such as a chloro group.

In formula (I), particular optionally substituted alkenyl or alkynyl groups for $R^1$ or $R^2$ are $C_{2-4}$alkenyl or alkynyl groups such as ethenyl.

Suitable optional substituents for $R^1$ and $R^2$ where these are an optionally substituted alkyl, optionally substituted alkenyl or optionally substituted alkynyl groups are functional groups as defined above.

In a particular embodiment of the invention, one of the groups $R^1$ and $R^2$ is a group of subformula (i) and the other is alkyl or alkoxy. Suitable alkyl or alkoxy groups $R^1$ and $R^2$ contain from 3 to 12 carbon atoms, preferably from 7 to 10 carbon atoms.

In an alternative embodiment, both of the groups $R^1$ and $R^2$ are groups of sub-formula (i).

Within the sub-formula (i), m is preferably 1. Furthermore, it is preferred that p is an integer of from 3-10, such as 4.

When $R^7$ in the group of sub-formula (i) is a group of formula —$C_q X_{2q+1}$, X is always the same halogen and is preferably fluoro. Suitable integers for q are from 2 to 10, more suitably from 2 to 6, such as 4. Such compounds are particularly preferred where smectic A phase stabilization is required.

Suitably in the groups of sub-formula (ii), $R^8$, $R^9$, $R^{10}$, $R^{11}$ and $R^{12}$ are $C_{1-4}$alkyl groups such as methyl, ethyl or propyl, and most preferably methyl or ethyl. The integer k is suitably from 1 to 6, more suitably from 1-4 and preferably 1.

Preferably in the compounds of formula (I), n is 1. A particularly preferred example of the group A is a group of sub-formula (iii).

When n is 0, it is preferred that at least one group $R^1$ or $R^2$ is a group of sub-formula (i) wherein $R^7$ is a group of sub-formula —$C_q X_{2q+1}$ as this enhances liquid crystal properties. Some compounds were n is 0 may not have liquid crystal properties and so find applications as dopants in liquid crystal systems only.

Suitably, at least one of the rings in the compound of formula (I) carries one or more halo atoms and in particular fluoro atoms. Suitably, there are two fluorine atoms on the same ring. Thus preferably, either $R^3$ and $R^4$, or $R^5$ and $R^6$ or $R^{13}$ and $R^{14}$ (or equivalent moieties on alternative groups A) are both fluoro and the others are all hydrogen.

Where high melting and clearing points are required, it is preferred that m+p in the group of sub-formula (i) equals an odd number. Where there are even numbers of atoms between the $R^7$ group in sub-formula (i) and the ring structure to which it is attached, lower melting and clearing points are found.

Particular examples of compounds of formula (I) are set out in Tables 1-3.

TABLE 1

(IA) — structure: terphenyl with substituents $R^3, R^4$ on first ring; $R^5, R^6$ on middle ring; $R^{13}, R^{14}$ on third ring; $R^1$ and $R^2$ as terminal groups.

| No | $R^3$ | $R^4$ | $R^5$ | $R^6$ | $R^{13}$ | $R^{14}$ | $R^1$ | $R^2$ |
|----|-------|-------|-------|-------|----------|----------|-------|-------|
| 1 | F | F | H | H | H | H | $C_4F_9C_4H_8O-$ | $-OC_8H_{17}$ |
| 2 | H | H | F | F | H | H | $C_4F_9C_4H_8O-$ | $-OC_8H_{17}$ |
| 3 | H | H | H | H | F | F | $C_4F_9C_4H_8O-$ | $-OC_8H_{17}$ |
| 4 | H | H | F | F | H | H | $C_4F_9C_4H_8O-$ | $-C_9H_{19}$ |
| 5 | F | F | H | H | H | H | $H_3C-Si(CH_3)_2-O-Si(CH_3)_2-C_4H_8O-$ | $-OC_8H_{17}$ |
| 6 | H | H | F | F | H | H | $H_3C-Si(CH_3)_2-O-Si(CH_3)_2-C_4H_8O-$ | $-OC_8H_{17}$ |
| 7 | H | H | H | H | F | F | $H_3C-Si(CH_3)_2-O-Si(CH_3)_2-C_4H_8O-$ | $-OC_8H_{17}$ |
| 8 | H | H | F | F | H | H | $H_3C-Si(CH_3)_2-O-Si(CH_3)_2-C_4H_8O-$ | $-C_9H_{19}$ |

TABLE 2

(IB) — structure: biphenyl with substituents $R^3, R^4$ on first ring; $R^5, R^6$ on second ring; $R^1$ and $R^2$ as terminal groups.

| No | $R^3$ | $R^4$ | $R^5$ | $R^6$ | $R^1$ | $R^2$ |
|----|-------|-------|-------|-------|-------|-------|
| 9  | F | F | H | H | $H_{17}C_8O-$ | $-OC_4H_8C_4F_9$ |
| 10 | H | H | F | F | $C_4F_9C_4H_8O-$ | $-OC_4H_8C_4F_9$ |
| 11 | F | F | H | H | $C_4F_9C_4H_8O-$ | $-OC_8H_{17}$ |
| 12 | F | F | H | H | $C_9H_{19}-$ | $-OC_4H_8C_4F_9$ |
| 13 | F | F | H | H | $C_4F_9C_4H_8O-$ | $-OC_9H_{19}$ |
| 14 | F | F | H | H | $H_3C-Si(CH_3)_2-O-Si(CH_3)_2-C_4H_8O-$ | $-OC_8H_{17}$ |
| 15 | H | H | F | F | $H_3C-Si(CH_3)_2-O-Si(CH_3)_2-C_4H_8O-$ | $-OC_8H_{17}$ |
| 16 | H | H | F | F | $H_3C-Si(CH_3)_2-O-Si(CH_3)_2-C_4H_8O-$ | $-OC_4H_8C_4F_9$ |

TABLE 2-continued (IB)

Structure: biphenyl with $R^3, R^4, R^5, R^6$ substituents, $R^1$ and $R^2$ terminal groups.

| No | $R^3$ | $R^4$ | $R^5$ | $R^6$ | $R^1$ | $R^2$ |
|---|---|---|---|---|---|---|
| 17 | F | F | H | H | $H_3C-Si(CH_3)_2-O-Si(CH_3)_2-C_4H_8O-$ | $-OC_4H_8C_4F_9$ |
| 18 | F | F | H | H | $C_4F_9C_4H_8O-$ | methyl (2S,3S)-2-chloro-3-methylpentanoate ester group |
| 19 | H | H | F | F | $C_4F_9C_4H_8O-$ | methyl (2S,3S)-2-chloro-3-methylpentanoate ester group |
| 20 | H | H | H | H | $C_4F_9C_{11}H_{22}O-$ | new get,511 |

TABLE 3

(IC)

Structure: biphenyl with $R^3, R^4, R^5, R^6$ substituents, $R^1$ group, and 1,3-dioxane with $R^2$ substituent.

| No | $R^3$ | $R^4$ | $R^5$ | $R^6$ | $R^1$ | $R^2$ |
|---|---|---|---|---|---|---|
| 21 | F | F | H | H | $H_3C-Si(CH_3)_2-O-Si(CH_3)_2-C_4H_8O-$ | $-C_9H_{19}$ |
| 22 | F | F | H | H | $C_4F_9C_4H_8O-$ | $-C_9H_{19}$ |

Compounds of formula (I) are suitably prepared by using conventional methods. In general they may be prepared by coupling together appropriately substituted ring systems or by derivatising a core ring structure. For example, they may be prepared by coupling a compound of formula (IV)

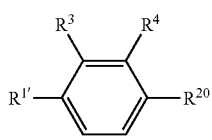

(IV)

where $R^3$ and $R^4$ are as defined in relation to formula (I) and $R^{1'}$ is a group $R^1$ as defined in relation to formula (I) or a precursor thereof, and $R^{20}$ is a reactive group such as boronic acid $B(OH)_2$, with a compound of formula (V)

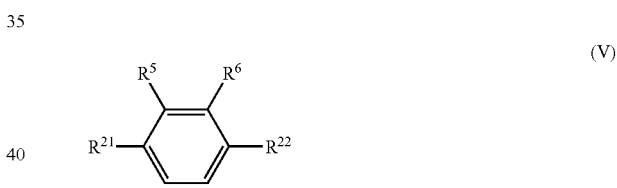

(V)

where $R^5$ and $R^6$ are as defined in relation to formula (I), $R^{22}$ is a group $(A)_n$-$R^{2'}$ where A and n are as defined in relation to formula (I) and $R^{2'}$ is a group $R^2$ as defined in relation to formula (I) or a precursor thereof, and $R^{21}$ is a leaving group such as halo, and in articular bromide. The reaction is suitably effected in the presence of a coupling agent such as $Pd(PPh_3)_4$ in an organic solvent such a dimethoxyethane (DME) and in the presence of a base such as an alkali metal carbonate such as $Na_2CO_3$.

Alternatively, where n is 1, compounds of formula (I) can be prepared by reacting a compound of formula (VI)

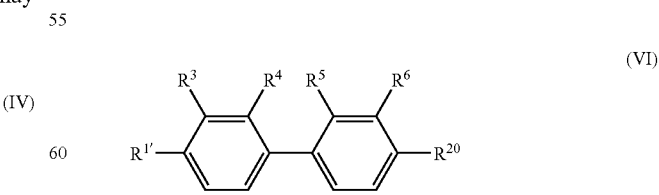

(VI)

where $R^3$, $R^4$, $R^5$ and $R^6$ are as defined in relation to formula (I), and $R^{1'}$ and $R^{20}$ are as defined in relation to formula (IV) with a compound of formula (VII)

$R^{22}$-A-$R^{2'}$ (VII)

where A is as defined in relation to formula (I) and $R^{2'}$ and $R^{2'}$ are as defined in relation to formula (V).

Suitable precursor groups $R^{1'}$ and $R^{2'}$ may for example be hydroxy groups, which can then be derivatised in one or more stages to form alkoxy groups or groups of sub-formula (i). The chemistry employed in such reactions is largely conventional and is illustrated in the examples hereinafter.

Compounds of formula (IV), (V), (VI) and (VII) are either known compounds or they can be prepared from known compounds by conventional methods.

Many of the compounds of formula (I) have liquid crystal properties and may be Smectic C compounds. In particular however, compounds of formula (I) may be smectic A type compounds. Thus they may be used in a variety of liquid crystal devices including liquid crystal display cells such as ferroelectric liquid crystal displays, and in particular smectic liquid crystal displays such as surface stabilised ferroelectric liquid crystal (SSFLC) displays.

Such devices form a further aspect of the invention.

The liquid crystal compounds of the invention may be used alone or in admixture with other liquid crystal compounds which may or may not comprise compounds of formula (I).

Such mixtures form a further aspect of the invention.

In particular compounds of formula (I) may be added to liquid crystal mixtures in order to stabilize the smectic A phase thereof.

In yet a further aspect, the invention comprises the use of a compound of formula (I) as a smectic A stabilizing additive in a liquid crystal mixture.

The invention will now be particularly described by way of example with reference to the following Preparations and Examples.

Preparation 1

A. 3-Iodo-5,5,6,6,7,7,8,8,8-nonafluorooct-3-en-1-ol

A mixture of sodium hydrosulfite (85%) (20.5 g, 0.1 mol) and sodium hydrogen carbonate (8.4 g, 0.1 mol) was added into a mixture of perfluorobutyl iodide (34.6 g, 0.1 mol), 3-butyn-1-ol (7.0 g, 0.1 mol), water (172 cm$^3$) and acetonitrile (200 cm$^3$). After the addition, the mixture was continuously irradiated with ultrasound (ca. 30° C.), until GLC analysis revealed a complete reaction (ca. 4 h). After adding water (180 cm$^3$) to dissolve the solid, the crude product was extracted into diethyl ether (3×100 cm$^3$) and dried (MgSO$_4$). The solvent was removed in vacuo and the pure product was obtained by reduced pressure distillation as a colourless liquid.

Yield=29 g (70%); bp. 118-120° C./0.1 mmHg.

$\delta_H$ (270 MHz; CDCl$_3$; Me$_4$Si): 1.51 (1H, s, OH), 2.94 (2H, t, J 6.3, OCH$_2$CH$_2$), [2H, 3.85 (t, J 5.7) 3.87 (t, J 6.2), OCH$_2$], [1H, 6.41 (t, J 13.0, Z=CZ), 6.49 (t, J 14.5, E=CH)]. $\nu_{max}$(film)/cm$^{-1}$: 3600-3100 (bonded O—H str), 2942 (—CH$_2$—, C—H asym str), 2888 (—CH$_2$—, C—H sym str), 1630 (C=C str), 1350 (O—H in-plane def), 1230 (C—F str), 1132 and 1044 (C—O str), 877,739. m/z: 416 [M]$^+$, 386, 366.

Several homologues of the series were prepared using analogous methods. The yields and analyses are detailed below.

B. 4-Iodo-6,6,7,7,8,8,9,9,9-nonafluorononan-1-ol

Yield=26 g (60%); bp. 68-72° C./0.15 mmHg.

$\delta_H$ (270 MHz; CDCl$_3$; Me$_4$Si): 1.66 (2H, m, OCH$_2$CH$_2$), 1.90 (2H, m, CHI CH$_2$), 2.86 (2H, m, CF$_2$CH$_2$), 3.69 (2H, t, J 6.0, OCH$_2$), 4.37 (1H, m, CHI). $\nu_{max}$(film)/cm$^{-1}$: 3600-3020 (bonded O—H str), 2940 (—CH$_2$—, C—H asym str), 2878 (—CH$_2$—, C—H sym str), 1350 (O—H in-plane def), 1230 (C—F str), 1133 and 1043 (C—O str), 878, 735, 725, 512 (C—I). m/z: 432 [M]$^+$, 431, 415, 305.

C. 5-Iodo-7,7,8,8,9,9,10,10,10-nonafluorodecan-1-ol

Crude product without distillation. Yield=45 g (~100%)

$\delta_H$ (270 MHz; CDCl$_3$; Me$_4$Si): 1.64 (4H, m, C$_2$H$_4$), 1.84 (2H, m, CHICH$_2$), 2.86 (2H, m, CF$_2$CH$_2$), 3.69 (2H, t, J 6.0, OCH$_2$), 4.34 (1H, m, CHI). $\nu_{max}$(film)/cm$^{-1}$: 3600-3010 (bonded O—H str), 2938 (—CH$_2$—, C—H asym str), 2864 (—CH$_2$—, C—H sym str), 1348 (O—H in-plane def), 1220 (C—F str), 1130 and 1070 (C—O str), 878, 722, 510 (C—I). m/z: 429 [M-OH]$^+$, 401, 319, 301.

D. 10-Iodo-12,12,13,13,14,14,15,15,15-nonafluoroentadecan-1-ol

Crude product without distillation. Yield=25.6 g (99%)

$\delta_H$ (270 MHz; CDCl$_3$; Me$_4$Si): 1.32 (12H, m, C$_6$H$_{12}$), 1.44 (1H, s, OH), 1.56 (2H, m, OCH$_2$CH$_2$), 1.79 (2H, m, CHICH$_2$),2.85 (2H, m, CF$_2$CH$_2$), 3.65 (2H, t, J 6.7, OCH$_2$), 4.33 (1H, tt, J 8.0 and 5.0, CHI). $\nu_{max}$(film)/cm$^{-1}$: 3600-3100 (bonded O—H str), 2926 (—CH$_2$—, C—H asym str), 2854 (—CH$_2$—, C—H sym str), 1350 (O—H in-plane def), 1234 and 1214 (C—F str), 1133 (C—O str), 758. m/z: 515 [M–1]$^+$, 499, 459, 443, 429, 415, 387.

E. 10-Iodo-12,12,13,13,14,14,15,15,16,16,17,17,17-tridecafluorohentadecan-1-ol

Crude product without distillation Yield=7.5 g (61%)

$\delta_H$ (270 MHz; CDCl$_3$; Me$_4$Si): 1.32 (12H, m, C$_6$H$_{12}$), 1.57 (2H, F OCH$_2$CH$_2$), 1.79 (2H, m, CHICH$_2$), 2.85 (2H, m, CF$_2$CH$_2$), 3.65 (2H, t, J 6.7, OCH$_2$), 4.33 (1H, tt, J 8.0 and 5.0, CHI). $\nu_{max}$(film)/cm$^{-1}$: 3600-3100 (bonded O—H str), 2930 (—CH$_2$—, C—H asym str), 2856 (—CH$_2$—, C—H sym str), 1359 (O—H in-plane def), 1237 and 1204 (C—F str), 1143 (C—O str), 760. m/z: 615 [M–1]$^+$, 599, 543, 487.

Preparation 2

A 5,5,6,6,7,7,8,8-Nonafluorooctan-1-ol

A mixture of 3-iodo-5,5,6,6,7,7,8,8,8-nonafluorooct-3-1-ol (Preparation 1A, 29 g, 0.07 mol), platinum oxide (1 g), triethylamine (14.1 g, 0.14 mol) and ethyl acetate (110 cm$^3$) was stirred overnight under an atmosphere of hydrogen at room temperature (a triethylamine-hydrogen iodide salt was formed which precipitated out as a white solid from the solution). The catalyst and the solid were removed by filtration and the solid was washed with ethyl acetate (2×50 cm$^3$). The combined organic phase was washed with 1% HCl (100 cm$^3$) followed by a saturated NaCl solution (50 cm$^3$), and then dried (MgSO$_4$). The solvent was removed in vacuo and the pure product was obtained by reduced pressure distillation as a colourless liquid.

Yield=18 g (87%); bp. 44-46° C./0.3 mmHg. $\delta_H$ (270 MHz; CDCl$_3$; Me$_4$Si): 1.39 (1H, s, OH), 1.69 (4H, m, C$_2$H$_4$), 2.12 (2H, m, CF$_2$CH$_2$), 3.71 (2H, t, J 6.0, OCH$_2$). $\nu_{max}$(film)/cm$^{-1}$: 3600-3020 (bonded O—H str), 2948 (—CH$_2$—, C—H asym str), 2880 (—CH$_2$—, C—H sym str), 1460 (—CH$_2$— sci, C—H del), 1351 (O—H in-plane def), 1228 (C—F str), 1128 and 1037 (C—O str), 877. m/z: 292 [M]$^+$, 291, 275, 254.

B. 6,6,7,7,8,8,9,9,9-Nonafluorononan-1-ol

A solution of AIBN (4.9 g, 30 mmol) in dioxane (150 cm$^3$) was added dropwise into a solution of 4iodo-6,6,7,7,8,8,9,9,9-nonafluorononan-1-ol (Preparation 1B, 25 g, 58 mmol), phosphorous acid (19.1 g, 0.29 mol) and triethylamine (32.3 g, 0.32 mol) in dioxane (150 cm$^3$) under an atmosphere of nitrogen during reflux. After addition, the reaction mixture was refluxed for a period of time until the GLC analysis revealed a complete reaction (usually an hour). The crude product was extracted into diethyl ether (3×50 cm$^3$) and dried (MgSO$_4$). The solvent was removed in vacuo and the pure product was obtained by reduced pressure distillation as a colourless liquid.

Yield=13.4 g (75%); bp. ~80° C./0.2 mmHg.

$\delta_H$ (270 MHz; CDCl$_3$; Me$_4$Si): 1.30 (1H, s, OH), 1.68-1.44 (6H, m, C$_3$H$_6$), 2.08 (2H, m, CF$_2$CH$_2$), 3.68 (2H, t, J 6.5, OCH$_2$). $\nu_{max}$(film)/cm$^{-1}$: 3600-3020 (bonded O—H str), 2942 (—CH$_2$—, C—H asym str), 2870 (—CH$_2$—, C—H sym str), 1462 (—CH$_2$— sci C—H def), 1352 (O—H in-plane del), 1225 (C—F str), 1130 and 1040 (C—O str), 877, 733, 716. m/z: 306 [M]$^+$, 305, 289.

Several homologues of the series were prepared using analogous methods. The yields and analyses are detailed below.

C. 7,7,8,8,9,9,10,10,10-Nonafluorodecan-1-ol

Yield=26 g (82%); bp. 68-70° C./0.2 mmHg.

$\delta_H$ (270 MHz; CDCl$_3$; Me$_4$Si): 1.30 (1H, s, OH), 1.42 (4H, m, C$_2$H$_4$), 1.60 (4H, m, CF$_2$CH$_2$CH$_2$, OCH$_2$CH$_2$), 2.06 (2H, m, CF$_2$CH$_2$), 3.66 (2H, t, J 6.5, OCH$_2$). $\nu_{max}$(film)/cm$^{-1}$: 3600-3020 (bonded O—H str), 2936 (—CH$_2$—, C—H asym str), 2860 (—CH$_2$—, C—H sym str), 1459 (—CH$_2$— sci, C—H def), 1350 (O—H in-plane def), 1248 (C—F str), 1129 and 1045 (C—O str), 877, 717. m/z: 319 [M-1]$^+$, 302, 274.

D. 12,12,13,13,14,14,15,15,15-Nonafluoropentadecan-1-ol

Yield=17.5 g (90%/o); bp. 76-80° C. /0.05 mmHg, mp. 36-38° C.

$\delta_H$ (270 MHz; CDCl$_3$; Me$_4$Si): 1.30 (14H, m, C$_7$H$_{14}$), 1.45 (1H, s, OH), 1.57 (4H, m, CF$_2$CH$_2$CH$_2$, OHCH$_2$CH$_2$, 2.05 (2H, m, CF$_2$CH$_2$), 3.64 (2H, t, J 6.7, OCH$_2$). $\nu_{max}$(KBr disc)/cm$^{-1}$: 3600-3100 (bonded O—H str), 2926 (—CH$_2$—, C—H asym str), 2856 (—CH$_2$—, C—H sym str), 1463 (—CH$_2$— sci, C—H def), 1353 (O—H in-plane def), 1220 (C—F str), 1130 and 1049 (C—O str), 880. m/z: 372 [M-H$_2$O]$^+$, 344.

E. 12,12,13,13,14,14,15,15,16,16,17,17,17-Tridecafluoroheptadecan-1-ol

Yield=5.4 g (92%); bp. 100-102° C. /0.2 mmHg, mp. 49-51° C.

$\delta_H$ (270 MHz; CDCl$_3$; Me$_4$Si): 1.29 (14H, m, C$_7$H$_{14}$), 1.54 (4H, m, CF$_2$CH$_2$CH$_2$, OCH$_2$CH$_2$), 2.06 (2H, m, CF$_2$CH$_2$), 3.64 (2H, t, J 6.7, OCH$_2$). $\nu_{max}$(KBr disc)/cm$^{-1}$: 3600-3160 (bonded O—H str), 2920 (—CH$_2$—, C—H asym str), 2848 (—CH$_2$—, C—H sym str), 1462 (—CH$_2$— sci, C—H def), 1364 (O—H in-plane def), 1226 and 1199 (C—F str), 1137 (C—O str), 788, 717. m/z: 472 [M-H$_2$O]$^+$, 444.

Preparation 3

A. 4-Bromo-1-(5,5,6,6,7,7,8,8,8-nonafluorooctyloxy)benzene

A solution of diethyl azodicarboxylate (3.5 g, 20 mmol) in dry diethyl ether (20 cm$^3$) was added dropwise into a stirred solution of 5,5,6,6,7,7,8,8,8-nonafluorooctan-1-ol (Preparation 2A, 5.8 g, 20 mmol), 4-bromophenol (3.5 g, 20 mmol) and triphenylphosphine (5.3 g, 20 mmol) in dry diethyl ether (50 cm$^3$) at room temperature.

The reaction mixture was stirred overnight at room temperature. The solvent was removed in vacuo and the pure product was obtained by flash column chromatography (dichloromethane) as a colourless liquid.

Yield=8 g (90%).

$\delta_H$ (270 MHz; CDCl$_3$; Me$_4$Si): 1.85 (4H, m, C$_2$H$_4$), 2.15 (2H, m, CF$_2$CH$_2$), 3.96 (2H, t, J 5.8, OCH$_2$), 6.77 (2H, AA'BB', C$_6$H$_4$), 7.37 (2H, AA'BB', C$_6$H$_4$). $\nu_{max}$(film)/cm$^{-1}$: 2946 (—CH$_2$—, C—H asym str), 2876 (—CH$_2$—, C—H sym str), 1588 and 1486 (C=C str), 1468 (—CH$_2$— sci, C—H def), 1240 (C—F and aryl-O str), 1131 (C—O str), 879, 822 (C—H o.o.p.d.). m/z: 448, 446 [M]$^+$, 174, 172.

B. 4-Bromo-4'-(5,5,6,6,7,7,8,8,8-nonafluorooctyloxy)biphenyl

Quantities: diethyl azodicarboxylate (3.5 g, 20 mmol), 5,5,6,6,7,7,8,8,8-nonafluorooctan-1-ol (Preparation 2A, 5.8 g, 20 mmol), 4'-bromo-4-hydroxybiphenyl (5.0 g, 20 mmol) and triphenylphosphine (5.3 g, 20 mmol). The experimental procedure was described in Preparation 3A.

Yield=9.5 g (91%); mp. 146-148° C.

$\delta_H$ (270 MHz; CDCl$_3$; Me$_4$Si): 1.88 (4H, m, C$_2$H$_4$), 2.18 (2H, m, CF$_2$CH$_2$), 4.04 (2H, t, J 5.7, OCH$_2$), 6.96 (2H, AA'BB', OC$_6$H$_4$), 7.41 (2H, AA'BB', C$_6$H$_4$), 7.48 (2H, AA'BB', C$_6$H$_4$), 7.53 (2H, AA'BB', C$_6$H$_4$). $\nu_{max}$(KBr disc)/cm$^{-1}$: 2924 (—CH$_2$—, C—H asym str), 2872 (—CH$_2$—, C—H sym str), 1603, 1517 and 1480 (C=C str), 1220 (C—F and aryl-O str), 1132 (C—O str), 880, 813 (C—H o.o.p.d.). m/z: 524, 522 [M]$^+$, 250, 248.

C. 2,3-Difluoro-4,5,5,6,6,7,7,8,8,8-nonafluorooctyloxy)benzene

Quantities: diethyl azodicarboxylate (9.14 g, 52.5 mmol), 5,5,6,6,7,7,8,8,8-nonafluorooctan-1-ol (Preparation 2A, 15.34 g, 52.5 mmol), 2,3-difluorophenol (6.83 g, 52.5 mmol) and triphenylphosphine (13.77 g, 52.5 mmol). The experimental procedure was described previously in Preparation 3A.

Yield=22 g (86%).

$\delta_H$ (270 M CDCl$_3$; Me$_4$Si): 1.89 (4H, m, C$_2$H$_4$), 2.18 (2H, m, CF$_2$CH$_2$), 4.08 (2H, t, J 6.0, OCH$_2$), 6.83-6.69 (2H, ABCXY, C$_6$F$_2$H$_3$), 7.02-6.93 (1H, ABCXY, C$_6$F$_2$H$_3$). $\nu_{max}$(film)/cm$^{-1}$: 2952 (—CH$_2$—, C—H asym str), 2884 (—CH$_2$—, C—H sym str), 1616, 1512 and 1480 (C=C str), 1222 (C—F and aryl-O str), 1132 and 1086 (C—O str), 879, 767 and 715 (C—H o.o.p.d.). m/z: 404 [M]$^+$, 385, 130.

Preparation 4

A. 2,3-Difluoro-4-(5,5,6,6,7,7,8,8,8-nonafluorooctyloxy)phenylboronic acid n-Butyllithium (5.5 cm$^3$, 10.0 M in hexanes, 55 mmol) was added dropwise to a stirred, cooled (−78° C.) solution of 2,3-difluoro-4-(5,5,6,6,7,7,8,8,8-nonafluorooctyloxy)benzene (Preparation 3C, 21.5 g, 53 mmol) in dry THF (200 cm$^3$) under an atmosphere of dry nitrogen. The reaction mixture was stirred (2.5 h) then a solution of trimethyl borate (11.4 g, 0.11 mol) in dry THF (30 cm$^3$) was added dropwise at −78° C. The reaction mixture was allowed to warm to room temperature overnight then stirred (1 h) with hydrochloric acid (10%, 30 cm$^3$). The product was extracted into diethyl ether (2×50 cm$^3$), and the combined extracts washed with water and dried (MgSO$_4$). The solvent was removed in vacuo to yield colourless crystals.

Yield=24 g (100%).

$\delta_H$ (270 MHz; DMSO; Me$_4$Si): 1.71 (2H, m, CF$_2$CH$_2$CH$_2$), 1.86 (2H, m, OCH$_2$CH$_2$), 2.33 (2H, m, CF$_2$CH$_2$), 4.13 (2H, t, J 6.1, OCH$_2$), 6.97 (1H, ABXY, OC$_6$F$_2$H$_2$), 7.32 (1H, ABXY, C$_6$F$_2$H$_2$), 8.15 (2H, br, OH). $\nu_{max}$(KBr disc)/cm$^{-1}$: 3700-3020 (bonded O—H str), 2960 (—CH$_2$—, C—H asym str), 2886 (—CH$_2$—, C—H sym str), 1625 and 1515 (C═C str), 1463 (—CH$_2$— sci, C—H def), 1355 (B—O str), 1240 (C—F and aryl-O str), 1138, 1080 and 1028 (C—O str), 883 (C—H o.o.p.d.). m/z: 404 [M-44, —B(OH)$_2$]$^+$, 386.

Preparation 5

2,3-Difluoro-4'-(5,5,6,6,7,7,8,8,8-nonafluorooctyloxy)biphenyl

A mixture of 4-bromo-1-(5,5,6,6,7,7,8,8,8-nonafluorooctyloxy)benzene (Preparation 3A, 2.24 g, 5 mmol), 2,3-difluorophenylboronic acid (0.95 g, 6 mmol), tetrakis(triphenylphosphine)palladium(0) (174 mg, 0.15 mmol), aqueous sodium carbonate (2 mol cm$^{-3}$, 5 cm$^3$) and 1,2-dimethoxyethane (30 cm$^3$) was heated under reflux for a period of time until the GLC analysis revealed a complete reaction (ca. 23 h) then cooled to room temperature. The mixture was extracted with diethyl ether (2×50 cm$^3$), and the ethereal extracts were washed with saturated aqueous sodium chloride (2×50 cm$^3$) and dried (Na$_2$SO$_4$). The solvent was removed in vacuo and the product was purified by flash column chromatography (dichloromethane/light petrol).

Yield=2.1 g (87%); mp. 51-53° C.

$\delta_H$ (270 MHz; CDCl$_3$; Me$_4$Si): 1.89 (4H, m, C$_2$H$_4$), 2.18 (2H, m, CF$_2$CH$_2$), 4.06 (2H, t, J 5.7, OCH$_2$), 6.98 (2H, AA'BB', OC$_6$H$_4$), 7.13 (3H, ABCXY, C$_6$F$_2$H$_3$), 7.48 (2H, AA'BB', C$_6$H$_4$). $\nu_{max}$(KBr disc)/cm$^{-1}$: 2950 (—CH$_2$—, C—H asym str), 2878 (—CH$_2$—, C—H sym str), 1603, 1588 and 1514 (C═C str), 1470 (—CH$_2$— sci, C—H def), 1272, 1261, 1196 and 1163 (C—F and aryl-O str), 1127 and 1042 (C—O str), 838, 788 and 721 (C—H o.o.p.d.). m/z: 480 [M]$^+$, 206.

Preparation 6

2,3-Difluoro-4'-(5,5,6,6,7,7,8,8,8-nonafluorooctyloxy)biphenyl-4-ylboronic acid Quantities: n-butyllithium (2 cm$^3$, 2.5 M in hexanes, 5 mmol), 2,3-difluoro-4'-(5,5,6,6,7,7,8,8,8-nonafluorooctyloxy)biphenyl (Preparation 5, 2 g, 4.2 mmol) and trimethyl borate (0.87 g, 8.4 mmol). The experimental procedure was described previously in Preparation 4.

Yield=2.2 g (100%).

$\delta_H$ (270 MHz; DMSO; Me$_4$Si): 1.73 (2H, m, CF$_2$CH$_2$CH$_2$), 1.86 (2H, m, OCH$_2$CH$_2$), 2.34 (2H, m, CF$_2$CH$_2$), 4.08 (2H, t, J 6.2, OCH$_2$), 7.06 (2H, AA'BB', OC$_6$H$_4$), 7.26 (1H, ABXY, OC$_6$F$_2$H$_2$), 7.38 (1H, ABXY, C$_6$F$_2$H$_2$), 7.51 (2H, AA'BB', C$_6$H$_4$), 8.38 (2H, s, OH). $\nu_{max}$(KBr disc)/cm$^{-1}$: 3700-3000 (bonded O—H str), 2960 (—CH$_2$—, C—H asym str), 2874 (—CH$_2$—, C—H sym str), 1605 and 1518 (C═C str), 1449 (—CH$_2$— sci C—H def), 1353 (B—O str), 1218 (C—F and aryl-O str), 1127 and 1028 (C—O str), 912, 881, 821 (C—H o.o.p.d.). m/z: 525 [M]$^+$, 508, 480.

Preparation 7

2,3-Difluoro-4'-5,5,6,6,7,7,8,8,8-nonafluorooctyloxy)-4-hydroxybiphenyl

Hydrogen peroxide (10%, 5 cm$^3$) was added dropwise to a stirred solution of 2,3-difluoro-4'-(5,5,6,6,7,7,8,8,8-nonafluorooctyloxy)biphenyl-4-ylboronic acid (Preparation 6, 1.47 g, 2.8 mmol) in diethyl ether (20 cm$^3$), heated under reflux. The stirred mixture was heated under reflux for a further 2.5 h, and then cooled. The ethereal layer was separated and the aqueous layer extracted with diethyl ether (2×30 cm$^3$). The combined ethereal layers were washed with water and dried (NgSO$_4$). The solvent was removed in vacuo and the product was purified by flash column chromatography (dichloromethane).

Yield=1.2 g (86%); mp. 112.0-112.5° C.

$\delta_H$ (270 MHz; CDCl$_3$; Me$_4$Si): 1.88 (4H, m, C$_2$H$_4$), 2.18 (2H, m, CF$_2$CH$_2$), 4.04 (2H, t, J 5.7, OCH$_2$), 5.15 (1H, s, OH), 6.83 (1H, ABXY, OC$_6$F$_2$H$_2$), 6.96 (2H, AA'BB', OC$_6$H$_4$), 7.05 (1H, ABXY, C$_6$F$_2$H$_2$), 7.42 (2H, AA'BB', C$_6$H$_4$). $\nu_{max}$(KBr disc)/cm$^{-1}$: 3600-3100 (bonded O—H str), 2950 (—CH$_2$—, C—H asym str), 2876 (—CH$_2$—, C—H sym str), 1604 and 1497 (C═C str), 1470 (—CH$_2$— sci, C—H def), 1243 (C—F and aryl-O str), 1126 and 1020 (C—O str), 848, 836 (C—H o.o.p.d.), 771. m/z: 496 [M]$^+$, 477, 460.

Preparation 8

2,3-Difluoro-4-(5,5,6,6,7,7,8,8,8-nonafluorooctyloxy)-4'-(2-tetrahydropyranyloxy)biphenyl Quantities: 4-bromo-1-(2-tetrahydropyranyloxy)benzene (2.57 g, 10 mmol), 2,3difluoro-4-(5,5,6,6,7,7,8,8,8-nonafluorooctyloxy)phenylboronic acid (Preparation 4), 4.93 g, 11 mmol), tetrakis(triphenylphosphine)palladium(0) (348 mg, 0.3 mmol) and aqueous sodium carbonate (2 mol cm$^{-3}$, 10 cm$^3$). The experimental procedure was described previously in Preparation 5.

Yield=4.8 g (83%); mp. 73-75° C.

$\delta_H$ (270 MHz; CDCl$_3$; Me$_4$Si): 1.67 (3H, m, C$_5$H$_9$O), 1.90 (7H, m, C$_2$H$_4$, C$_5$H$_9$O), 2.20 (2H, m, CF$_2$CH$_2$), 3.63 (1H, m, 6-Ha), 3.93 (1H, m, 6-He), 4.11 (2H, t, J 5.7, OCH$_2$), 5.47 (1H, t, J 3.2, 2-H), 6.77 (1H, ABXY, OC$_6$F$_2$H$_2$), 7.07 (1H, ABXY, C$_6$F$_2$H$_2$), 7.12 (2H, AA'BB', OC$_6$H$_4$), 7.42 (2H, AA'BB', C$_6$H$_4$). $\nu_{max}$(KBr disc)/cm$^{-1}$: 2952 (—CH$_2$—, C—H asym str), 2876 (—CH$_2$—, C—H sym str), 1623, 1604 and 1501 (C═C str), 1466 (—CH$_2$— sci, C—H def), 1237 (C—F and aryl-O str), 1127 and 1078 (C—O str), 960, 918, 798 (C—H o.o.p.d.), 716. m/z: 581 [M+1]$^+$, 496, 477, 460.

Preparation 9

2,3-Difluoro-4-5,5,6,6,7,7,8,8,8-nonafluorooctyloxy)-4'-hydroxybiphenyl

A solution of 2,3-difluoro-4-(5,5,6,6,7,7,8,8,8-nonafluorooctyloxy)-4'-(2-tetrahydropyranyloxy)biphenyl (Preparation 8, 4.8 g, 8.3 mmol) and toluene-4-sulfonic acid monohydrate (0.1 g) in dichloromethane (20 cm$^3$) and methanol (30 cm$^3$) was stirred overnight at room temperature. The solution was diluted with diethyl ether, and washed with aqueous sodium bicarbonate (10 cm$^3$), water and dried (MgSO$_4$). The solvent was removed in vacuo and the product was purified by flash column chromatography (dichloromethane /light petrol).

Yield=3.9 g (95%); mp. 132-134° C.

$\delta_H$ (270 MHz; CDCl$_3$; Me$_4$Si): 1.90 (4H, m, C$_2$H$_4$), 2.20 (2H, m, CF$_2$CH$_2$), 4.11 (2H, t, J 5.7, OCH$_2$), 4.75 (1H, s, OH), 6.77 (1H, ABXY, OC$_6$F$_2$H$_2$), 6.90 (2H, AA'BB', OC$_6$H$_4$), 7.06 (1H, ABXY, C$_6$F$_2$H$_2$), 7.39 (2H, AA'BB', C$_6$H$_4$). $v_{max}$(KBr disc)/cm$^{-1}$: 3640-3200 (bonded O—H str), 2954 (—CH$_2$—, C—H asym str), 2880 (—CH$_2$—, C—H sym str), 1607 and 1502 (C=C str), 1471 (—CH$_2$— sci, C—H def), 1233 (C—F and aryl-O str), 1133 and 1078 (C—O str), 833 and 814 (C—H o.o.p.d.), 720. m/z: 496 [M]$^+$, 477, 222.

Preparation 10

2,3-Difluoro-4-octyloxy-4'-(2-tetrahydropyranyloxy)biphenyl

Quantities: 4-bromo-1-(2-tetrahydropyranyloxy)benzene (6.43 g, 25 mmol), 2,3-difluoro-4-octyloxyphenylboronic acid (8.58 g, 25 mmol), tetrakis(triphenylphosphine)palladium(0) (869 mg, 0.75 mmol) and aqueous sodium carbonate (2 mol cm$^{-3}$, 25 cm$^3$). The experimental procedure was described previously in Preparation 5.

Yield=9.1 g (87%); mp. 74-76° C. $\delta_H$ (270 MHz; CDCl$_3$; Me$_4$Si): 0.89 (3H, t, J 7.0, CH$_3$), 1.29 (8H, m, C$_4$N$_8$), 1.48 (2H, m, OCH$_2$CH$_2$CH$_2$),1.67 (3H, m, C$_5$H$_9$O), 1.87 (5H, m, OCH$_2$CH$_2$, C$_5$H$_9$O), 2.02 (1H, m, C$_5$H$_9$O), 3.63 (1H, m, 6-Ha), 3.93 (1H, m, 6-He), 4.06 (2H, t, J 6.5, OCH$_2$), 5.47 (1H, t, J 3.1, 2-H), 6.77 (1H, ABXY, OC$_6$F$_2$H$_2$), 7.05 (1H, ABXY, C$_6$F$_2$H$_2$), 7.11 (2H AA'BB', OC$_6$H$_4$), 7.42 (2H, AA'BB', C$_6$H$_4$). $v_{max}$(KBr disc)/cm$^{-1}$: 2942 (CH$_3$—, C—H asym str), 2924 (—CH$_2$—, C—H asym str), 2868 (—CH$_2$—, C—H sym str), 2852 (—CH$_2$—, C—H sym str), 1624, 1605 and 1497 (C=C str), 1470 (CH$_3$— asym, —CH$_2$— sci C—H def), 1296, 1237 (aryl-O str), 1199, 1179, 1112 and 1070 (C—O str), 964, 838 and 791 (C—H o.o.p.d), 716. m/z: 418 [M]$^+$, 334, 222.

Preparation 11

2,3-Difluoro-4-octyloxy-4"-(2-tetrahydropyranyloxy)-1,1':4',1"-terphenyl

Quantities: 4-bromo-4'-C2-tetrahydropyranyloxy)biphenyl (4.75 g, 14.3 mmol), 2,3-difluoro-4-octyloxyphenylboronic acid (5.1 g, 17.8 mmol), tetrakis(triphenylphosphine)palladium(0) (498 mg, 0.43 mmol) and aqueous sodium carbonate (2 mol cm$^{-3}$, 15 cm$^3$). The experimental procedure was described previously for Preparation 5.

Yield=5.5 g (78%); Mesomorphism (T/° C.): Cryst 105 (S$_C$ 82.4) N 133.9 Iso.

$\delta_H$ (270 MHz; CDCl$_3$; Me$_4$Si): 0.90 (3H, t, J 6.7, CH$_3$), 1.31 (8H, m, C$_4$H$_8$), 1.48 (2H, m, OCH$_2$CH$_2$CH$_2$), 1.68 (3H, m, C$_5$H$_9$O), 1.88 (7H, m, C$_2$H$_4$, C$_5$H$_9$O), 2.03 (1H, m, C$_5$H$_9$O), 3.64 (1H, m, 6-Ha), 3.95 (1H, m, 6-He), 4.08 (2H, t, J 6.5, OCH$_2$), 5.48 (1H, t, J 3.1, 2-H), 6.81 (1H, ABXY, OC$_6$F$_2$H$_2$), 7.14 (3H, m, OC$_6$H$_4$, C$_6$F$_2$H$_2$), 7.56 (4H, AA'BB', C$_6$H$_4$), 7.62 (2H, AA'BB', C$_6$H$_4$). $v_{max}$(KBr disc)/cm$^{-1}$: 2924 (CH$_3$—, —CH$_2$—, C—H asym str), 2852 (CH$_3$—, —CH$_2$—, C—H sym str), 1625, 1601 and 1492 (C=C str), 1465 (CH$_3$— asym, —CH$_2$— sci, C—H def), 1284 and 1243 (aryl-O str), 1197, 1178, 1107 and 1072 (C—O str), 909, 868 and 820 (C—H o.o.p.d.), 716. m/z: 495 [M+1]$^+$, 410, 298.

Preparation 12

2,3-Difluoro-4'-hydroxy-4-octyloxybiphenyl

Quantities: 2,3difluoro-4-octyloxy-4'-(2-tetrahydropyranyloxy)biphenyl (Preparation 10, 9.0 g, 21.5 mmol). The experimental procedure was described previously in Preparation 9.

Yield=6.3 g (88%); mp. 118-119° C.

$\delta_H$ (270 MHz; CDCl$_3$; Me$_4$Si): 0.89 (3H, t, J 6.8, CH$_3$), 1.29 (8H, m, C$_4$H$_8$), 1.48 (2H, m, OCH$_2$CH$_2$CH$_2$), 1.87 (2H, qn, J 7.0, OCH$_2$CH$_2$), 4.07 (2H, t, J 6.6, OCH$_2$), 4.89 (1H, s, OH), 6.77 (1H, ABXY, OC$_6$F$_2$H$_2$), 6.90 (2H, AA'BB', OC$_6$H$_4$), 7.05 (1H, ABXY, C$_6$F$_2$H$_2$), 7.38 (2H, AA'BB', C$_6$H$_4$). $v_{max}$(KBr disc)/cm$^{-1}$: 3640-3200 (bonded O—H str), 2954 (CH$_3$—, C—H asym str), 2922 (—CH$_2$—, C—H asym str), 2870 (—CH$_2$—, C—H sym str), 2854 (—CH$_2$—, C—H sym str), 1607, 1592 and 1501 (C=C str), 1470 (CH$_3$— asym, —CH$_2$— sci C—H def), 1255 (aryl-O str), 1077 (C—O str), 832 and 812 (C—H o.o.p.d.), 720. m/z: 334 [M]$^+$, 279, 250, 222.

Preparation 13

2,3-Difluoro-4"-hydroxy-4-octyloxy-1,1':4',1"-terphenyl

Quantities: 2,3-difluoro-4-octyloxy-4"-(2-tetrahydropyranyloxy)-1,1':4',1"-terphenyl (Preparation 11, 5.5 g, 11 mmol). The experimental procedure was described previously in Preparation 9.

Yield=4.4 g (97%/o); mp. 195.0-195.5° C.

$\delta_H$ (270 MHz; CDCl$_3$; Me$_4$Si): 0.90 (3H, t, J 6.6, CH$_3$), 1.30 (8H, m, C$_4$H$_8$), 1.49 (2H, m, OCH$_2$CH$_2$CH$_2$), 1.85 (2H, qn, J 7.0, OCH$_2$CH$_2$), 4.09 (2H, t, J 6.6, OCH$_2$), 4.85 (1H, s, OH), 6.81 (1H, ABXY, OC$_6$F$_2$H$_2$), 6.93 (2H, AA'BB', OC$_6$H$_4$), 7.14 (1H, ABXY, C$_6$F$_2$H$_2$), 7.53 (2H, AA'BB', C$_6$H$_4$), 7.56 (2H, AA'BB', C$_6$H$_4$), 7.61 (2H, AA'BB', C$_6$H$_4$). $v_{max}$(KBr disc)/cm$^{-1}$: 3600-3100 (bonded O—H str), 2952 (CH$_3$—, C—H asym str), 2918 (—CH$_2$—, C—H asym str), 2868 (CH$_3$—, C—H sym str), 2850 (—CH$_2$—, C—H sym str), 1629, 1607 and 1496 (C=C str), 1463 (CH$_3$— asym, —CH$_2$— sci, C—H def), 1320, 1300, 1254 (aryl-O str), 1106 and 1077 (C—O str), 802 (C—H o.o.p.d.). m/z: 410 [M]$^+$, 298.

Preparation 14

2,3-Difluoro-4-hydroxy-4'-octyloxybiphenyl

Quantities: hydrogen peroxide (10%, 10 cm$^3$) and 2,3-difluoro-4'-octyloxybiphenyl-4-ylboronic acid (1.81 g, 5 mmol). The experimental procedure was described previously in Preparation 7.

Yield=1.5 g (90%); mp. 99-101° C.

δ_H (270 MHz; CDCl₃; Me₄Si): 0.90 (3H, t, J 7.0, CH₃), 1.32 (8H, m, C₄H₈), 1.47 (2H, m, OCH₂CH₂CH₂), 1.81 (2H, m, OCH₂CH₂), 4.00 (2H, t, J 6.7, OCH₂), 5.16 (1H, s, OH), 6.85 (1H, ABXY, OC₆F₂H₂), 6.96 (2H, AA'BB', OC₆H₄), 7.05 (1H, ABXY, C₆F₂H₂), 7.41(2H, AA'BB', C₆H₄). ν_max (KBr disc)/cm⁻¹: 3640-3100 (bonded O—H str), 2956 (CH₃—, C—H asym str), 2934 and 2922 (—CH₂—, C—H asym str), 2872 (CH₃—, C—H sym str), 2856 (—CH₂—, C—H sym str), 1628, 1606 and 1497 (C═C str), 1462 (CH₃— asym, —CH₂— sci C—H def), 1284, 1260, 1245 (aryl-O str), 1087 and 1024 (C—O str), 892, 814 (C—H o.o.p.d.), 720. m/z: 334 [M]⁺, 318, 222.

Preparation 15

4-(3-Butenyloxy)-2,3-difluoro-4'-octyloxybiphenyl

Quantities: diethyl azodicarboxylate (0.26 g, 1.5 mmol), 3-buten-1-ol (0.11 g, 1.5 mmol), 2,3-difluoro-4-hydroxy-4'-octyloxybiphenyl (Preparation 14, 0.5 g, 1.5 mmol) and triphenylphosphine (0.39 g, 1.5 mmol). The experimental procedure was described previously in Preparation 3A Yield=0.5 g (86%); mp. 58-59° C.

δ_H (270 MHz; CDCl₃; Me₄Si): 0.89 (3H, t, J 6.6, CH₃), 1.31 (8H, m, C₄H₈), 1.47 (2H, m, OCH₂CH₂CH₂), 1.80 (2H, qn, J 7.0, OCH₂CH₂), 2.60 (2H, qt, J 6.7 and 1.3, CH₂—CH═CH₂), 3.99 (2H, t, J 6.5, OCH₂C₇H₁₅), 4.12 (2H, t, J 6.7, OCH₂), 5.14 (1H, ddt, J 10.0, 1.8 and 1.3, ZCH═CH₂), 5.19 (1H, ddt, J 17.0, 1.8 and 1.3, ECH═CH₂), 5.92 (1H, ddt, J 17.0, 10.0 and 6.7, CH═CH₂), 6.78 (1H, ABXY, OC₆F₂H₂), 6.96 (2H, AA'BB', OC₆H₄), 7.06 (1H, ABXY, C₆F₂H₂), 7.42(2H, AA'BB', C₆H₄). ν_max(KBr disc)/cm⁻¹: 3070 (═C—H str), 2948 (CH₃—, C—H asym str), 2916 (—CH₂—, C—H asym str), 2864 (CH₃—, C—H sym str), 2846 (—CH₂—, C—H sym str), 1627, 1609 and 1502 (C═C str), 1467 (CH₃-asym, —CH₂— sci, C—H def), 1299, 1288, 1273, 1250 (aryl-O str), 1106 and 1079 (C—O str), 892, 837 and 797 (C—H o.o.p.d.). m/z: 388 [M]⁺, 344, 276, 222.

Preparation 16

4'-(3-Butenyloxy)-2,3-difluoro-4-octyloxybiphenyl

Quantities: diethyl azodicarboxylate (0.26 g, 1.5 mmol), 3-buten-1-ol (0.11 g, 1.5 mmol), 2,3-difluoro-4'-hydroxy-4-octyloxybiphenyl (Preparation 12, 0.5 g, 1.5 mmol) and triphenylphosphine (0.39 g, 1.5 mmol). The experimental procedure was described previously in Preparation 3A Yield=0.4 g (69%); mp. 55-56° C.

δ_H (270 MH; CDCl₃; Me₄Si): 0.90 (3H, t, J 6.7, CH₃), 1.32 (8H, m, C₄H₈), 1.48 (2H, m, OCH₂CH₂CH₂), 1.84 (2H, qt, J 7.0, OCH₂CH₂), 2.57 (2H, qt, J 6.8 and 1.3, CH₂—CH═CH₂), 4.06 (4H, t, J 6.8, 2×OCH₂), 5.13 (1H, ddt, J 10.0, 1.8 and 1.3, ZCH═CH₂), 5.19 (1H, ddt, J 17.0, 1.8 and 1.3, ECH═CH₂), 5.92 (1H, ddt, J 17.0, 10.0 and 6.7, CH═CH₂), 6.77 (1H, ABXY, OC₆F₂H₂), 6.96 (2H, AA'BB', OC₆H₄), 7.05 (1H, ABXY, C₆F₂H₂), 7.42(2H, AA'BB', C₆H₄). ν_max(KBr disc)/cm⁻¹: 3084 (═C—H str), 2954 (CH₃—, C—H asym str), 2928 (—CH₂—, C—H asym str), 2874 (CH₃—, C—H sym str), 2854 (—CH₂—, C—H sym str), 1627, 1605 and 1501 (C═C str), 1463 (CH₃— asym, —CH₂— sci, C—H def), 1251 (aryl-O str), 1082 (C—O str), 800 (C—H o.o.p.d.). m/z: 388 [M]⁺, 362, 347, 334.

Preparation 17

4-(3-Butenyloxy)-2,3-difluoro-4''-octyloxy-1,1':4'1''-terphenyl

Quantities: diethyl azodicarboxylate (035 g, 2 mmol), 3-buten-1-ol (0.18 g, 2.5 mmol), 2,3 difluoro-4-hydroxy-4''-octyloxy-1,1':4',1''-terphenyl (0.82 g, 2 mmol) and triphenylphosphine (0.53 g, 2 mmol). The experimental procedure was described previously in Preparation 3A.

Yield=0.4 g (43%);

Mesomorphism (T/° C.): Cryst 120 S_C 161.8 S_A 179.0 N 181.2 Iso.

δ_H (270 MHz; CDCl₃; Me₄Si): 0.89 (3H, t, J 6.7, CH₃), 1.31 (8H, m, C₄H₈), 1.48 (2H, m, OCH₂CH₂CH₂), 1.81 (2H, qn, J 7.0, OCH₂CH₂), 2.62 (2H, qt, J 6.8 and 1.3, CH₂—CH═H₂), 4.01 (2H, t, J 6.6, OCH₂C₇H₁₅), 4.15 (2H, t, J 6.8, OCH₂), 5.15 (1H, ddt, J10.2, 1.7 and 1.3, ZCH═CH₂), 5.20 (1H, ddt, J 17.2, 1.7 and 1,3, ECH═CH₂), 592 (1H, ddt, J 17.2, 10.2 and 6.7, CH═CH₂), 6.82 (1H, ABXY, OC₆F₂H₂), 6.99 (2H, AA'BB', OC₆H₄), 7.14 (1H, ABXY, C₆F₂H₂), 7.56 (4H, AA'BB', C₆H₄), 7.62 (2H, AA'BB', C₆H₄). ν_max(KBr disc)/cm⁻¹: 3080 (═C—H str), 2955 (CH₃—, C—H asym str), 2934 and 2920 (—CH₂—, C—H asym str), 2872 (CH₃—, C—H sym str), 2854 (—CH₂—, C—H sym str), 1629, 1603 and 1496 (C═C str), 1465 (CH₃— asym, —CH₂— sci, C—H def), 1310, 1260, 1252 (aryl-O str), 1082 (C—O str), 802 (C—H o.o.p.d.). m/z: 464 [M]⁺, 409, 352.

Preparation 18

4''-(3-Butenyloxy)-2,3-difluoro-4-octyloxy-1,1':4',1''-terphenyl

Quantities: diethyl azodicarboxylate (0.23 g, 1.3 mmol), 3-buten-1-ol (0.11 g, 1.5 mmol), 2,3-difluoro-4''-hydroxy-4-octyloxy-1,1':4',1''-terphenyl (Preparation 13, 0.5 g, 1.2 mmol) and triphenylphosphine (0.34 g, 1.3 mmol). The experimental procedure was described previously in Preparation 3A.

Yield=0.4 g (72%); Mesomorphism(T/° C.): Cryst 118 S_C 138.1 S_A 161.7 N 171.4 Iso.

δ_H (270 MHz, CDCl₃; Me₄Si): 0.90 (3H, t, J 6.8, CH₃), 1.29 (8H, m, C₄H₈), 1.49 (2H, m, OCH₂CH₂CH₂), 1.85 (2H, qn, J 7.0, OCH₂CH₂), 2.58 (2H, qt, J 6.8 and 1.3, CH₂—CH═CH₂), 4.07 (2H, t, J 6.9, OCH₂C₇H₁₅), 4.08 (2H, t, J 6.7, OCH₂), 5.13 (1H, ddt, J 10.2, 1.7 and 13, ZCH═CH₂), 5.20 (1H, ddt, J 17.2, 1.7 and 1.3, ECH═CH₂), 5.94 (1H, ddt, J 17.2, 10.2 and 6.7, CH═CH₂), 6.81 (1H, ABXY, OC₆F₂H₂), 7.00 (2H, AA'BB', OC₆H₄), 7.14 (1H, ABXY, C₆F₂H₂), 7.56 (4H, AA'BB', C₆H₄), 7.63 (2H, AA'BB', C₆H₄). ν_max(KBr disc)/cm⁻¹: 3076 (═C—H str), 2950 (CH₃—, C—H asym str), 2916 (—CH₂—, C—H asym str), 2870 (CH₃—, C—H sym str), 2852 (—CH₂—, C—H sym str), 1628, 1602 and 1493 (C═C str), 1462 (CH₃13 asym, —CH₂— sci, C—H def), 1250 (aryl-O str), 1080 (C—O str), 827 and 798 (C—H o.o.p.d.). m/z: 464 [M]⁺, 438, 408.

Preparation 19

4-(3-Butenyloxy)-2',3'-difluoro-4''octyloxy-1,1':4',1''-terphenyl

Quantities: diethyl azodicarboxylate (0.23 g, 1.3 mmol), 3-buten-1-ol (0.11 g, 1.5 mmol), 2',3'-difluoro-4-hydroxy-4''-octyloxy-1,1':4',1''-terphenyl (0.5 g, 1.2 mmol) and triphenylphosphine (0.34 g, 1.3 mmol). The experimental procedure was described previously in Preparation 3A.

Yield=0.5 g (90%); Mesomorphism (T/° C.): Cryst 98 $S_C$ 101.6 N 161.8 Iso.

$\delta_H$ (270 MHz; CDCl$_3$; Me$_4$Si): 0.89 (3H, t, J 6.8, CH$_3$), 1.30 (8H, m, C$_4$H$_8$), 1.48 (2H, m, OCH$_2$CH$_2$CH$_2$), 1.82 (2H, qn, J 7.0, OCH$_2$CH$_2$), 2.58 (2H, qt, J 6.8 and 1.3, CH$_2$—CH=CH$_2$), 4.01 (2H, t, J 6.6, OCH$_2$C$_7$H$_{15}$), 4.08 (2H, t, J 6.7, OCH$_2$), 5.13 (1H, ddt, J 10.2, 1.7 and 1.3, ZCH=CH$_2$), 5.20 (1H, ddt, J 17.2, 1.7 and 1.3, ECH=CH$_2$), 5.93 (1H, ddt, J 17.2, 10.2 and 6.7, CH=CH$_2$), 7.00 (4H, AA'BB', OC$_6$H$_4$), 7.21 (2H, ABXY, C$_6$F$_2$H$_2$), 7.52 (4H, AA'BB', C$_6$H$_4$), 7.63 (2H, AA'BB', C$_6$H$_4$). $\nu_{max}$(KBr disc)/cm$^{-1}$: 3078 (=C—H str), 2950 (CH$_3$—, C—H asym str), 2928 and 2916 (—CH$_2$—, C—H asym str), 2866 (CH$_3$—, C—H sym str), 2850 (—CH$_2$—, C—H sym str), 1603, 1520 and 1481 (C=C str), 1467 and 1451 (CH$_3$— asym, —CH$_2$— sci, C—H def), 1287, 1250 and 1249 (aryl-O str), 1181 (C—O str), 812 (C—H o.o.p.d.). m/z: 464 [M]$^+$, 410, 365.

Preparation 20

4-(3-Butenyloxy)-2',3'-difluoro-4''-nonyl-1,1':4',1''-terphenyl

Quantities: diethyl azodicarboxylate (0.23 g, 1.3 mmol), 3-buten-1-ol (0.11 g, 1.5 mmol), 2',3'-difluoro-4-hydroxy-4''-nonyl-1,1':4',1''-terphenyl (0.5 g, 1.2 mmol) and triphenylphosphine (0.34 g, 13 mmol). The experimental procedure was described previously in Preparation 3A Yield=0.5 g (90%); Mesomorphism (T/° C.): Cryst 60 (S$_C$ 60.0) N 128.4 Iso.

$\delta_H$ (270 MHz; CDCl$_3$; Me$_4$Si): 0.89 (3H, t, J 6.7, CH$_3$), 1.28 (12H, m, C$_6$H$_{12}$), 1.66 (2H, qn, J 7.5, PhCH$_2$CH$_2$), 2.58 (2H qt, J 6.8 and 1.3, CH$_2$—CH=CH$_2$), 2.66 (2H, t, J 7.5, PhCH$_2$), 4.08 (2H t, J 6.8, OCH$_2$), 5.14 (1H, ddt, J 10.2, 1.7 and 1.3, ZCH=CH$_2$), 5.20 (1H, ddt, J 17.2, 1.7 and 1.3, ECH=CH$_2$), 5.93 (1H, ddt, J 17.2, 10.2 and 6.7, CH=CH$_2$), 7.00 (2H, AA'BB', OC$_6$H$_4$), 7.22 (2H, ABXY, C$_6$F$_2$H$_2$), 7.29 (2H, AA'BB', C$_6$H$_4$), 7.51 (4H, AA'BB', C$_6$H$_4$). $\nu_{max}$(KBr disc)/cm$^{-1}$: 3074 (=C—H str), 2948 (CH$_3$—, C—H asym str), 2912 (—CH$_2$—, C—H asym str), 2866 (CH$_3$—, C—H sym str), 2844 (—CH$_2$—, C—H sym str), 1603, 1520 and 1479 (C=C str), 1451 (CH$_3$— asym, —CH$_2$— sci, C—H def), 1400, 1244 (aryl-O str), 1175 and 1030 (C—O str), 818 (C—H o.o.p.d.). m/z: 462 [M]$^+$, 434, 421, 408.

Preparation 21

2-[4-(3-Butenyloxy)-2,3-difluorobiphenyl-4'yl]-5-nonyl-1,3-dioxane

Quantities: diethyl azodicarboxylate (0.19 g, 1.1 mmol), 3-buten-1-ol (0.08 g, 1.1 mmol), 2-(2,3-difluoro-4-hydroxybiphenyl-4'-yl)-5-nonyl-1,3dioxane (0.5 g, 1.2 mmol) and triphenylphosphine (0.34 g, 1.3 mmol). The experimental procedure was described previously in Preparation 3A.

Yield=0.5 g (~100%); Mesomorphism (T/° C.). Cryst 62 S$_A$ 104.0 N 122.9 Iso.

$\delta_H$ (270 MHz; CDCl$_3$; Me$_4$Si): 0.89 (3H, t, J 6.6, CH$_3$), 1.11 (2H, q, J 6.6, CH$_2$CH$_3$), 1.28 (14H, m, C$_7$H$_{14}$), 2.14 (1H, m, 5-H), 2.60 (2H, qt, J 6.7 and 1.3, CH$_2$—CH=CH$_2$), 2.66 (2H, t, J 7.5, PhCH$_2$), 3.55 (2H, dd, J 11.5 and 11.5, Ha), 4.13 (2H, t, J 6.7, OCH$_2$), 4.25 (2H, dd, J 11.5 and 4.5, He), 5.14 (1H, ddt, J 10.2, 1.8 and 1.3, ZCH=CH$_2$), 5.19 (1H, ddt, J 172, 1.8 and 1.3, ECH=CH$_2$), 5.45 (1H, s, 2-H), 5.92 (1H, ddt, J 17.2, 10.2 and 6.7, CH=CH$_2$), 6.79 (1H, ABXY, OC$_6$H$_2$F$_2$), 7.07 (1H, ABXY, C$_6$F$_2$H$_2$), 7.50 (2H, AA'BB', C$_6$H$_4$), 7.55 (2H, AA'BB', C$_6$H$_4$). $\nu_{max}$(KBr disc)/cm$^{-1}$: 3082 (=C—H str), 2954 (CH$_3$—, C—H asym str), 2924 (—CH$_2$—, C—H asym str), 2854 (CH$_3$—, —CH$_2$—, C—H sym str), 1630 and 1502 (C=C str), 1468 (CH$_3$— asym, —CH$_2$— sci, C—H def), 1391, 1314 (aryl-O sr), 1077 and 1026 (C—O str), 796 (C—H o.o.p.d.). m/z: 472 [M]$^+$, 471, 457, 431, 401.

Preparation 22

4'-(3-Butenyloxy)-2,3-difluoro-4-(5,5,6,6,7,7,8,8,8-nonafluorooctyloxy)biphenyl

Quantities: diethyl azodicarboxylate (0.57 g, 3.3 mmol), 3-buten-1-ol (0.24 g, 3.3 mmol), 2,3-difluoro-4'-hydroxy-4-(5,5,6,6,7,7,8,8,8-nonafluorooctyloxy)biphenyl (Preparation 9, 1.45 g, 2.9 mmol) and triphenylphosphine (0.87 g, 3.3 mmol). The experimental procedure was described previously in preparation 3A.

Yield=1.4 g (88%); Mesomorphism (T/° C.): Cryst 76 S$_A$ 83.6 Iso.

$\delta_H$ (270 MHz; CDCl$_3$; Me$_4$Si): 1.91 (4H, m, C$_2$H$_4$), 2.20 (2H, m, CF$_2$CH$_2$), 2.57 (2H, qt, J 6.6 and 1.3, CH$_2$—CH=CH$_2$), 4.00 (2H, t, J 6.6, OCH$_2$Rf), 4.11 (2H, t, J 5.7, OCH$_2$), 5.13 (1H, ddt, J 10.5, 1.7 and 1.3, ZCH=CH$_2$), 5.19 (1H, ddt, J 17.0, 1.7 and 1.3, ECH=CH$_2$), 5.92 (1H, ddt, J 17.0, 10.5 and 6.6, CH=CH$_2$), 6.77 (1H, ABXY, OC$_6$F$_2$H$_2$), 6.97 (2H, AA'BB', OC$_6$H$_4$), 7.07 (1H, ABXY, C$_6$F$_2$H$_2$), 7.42 (2H, AA'BB', C$_6$H$_4$). $\nu_{max}$(KBr disc)/cm$^{-1}$: 3084 (=C—H str), 2944, (—CH$_2$—, C—H asym str), 2868 (—CH$_2$—, C—H sym str), 1625, 1604 and 1502 (C=C str), 1467 (—CH$_2$— sci, C—H def), 1353, 1217 (C—F and aryl-O str), 1129 and 1080 (C—O str), 880, 838 and 797 (C—H o.o.p.d.). m/z: 550 [M]$^+$, 496, 222.

Preparation 23

4-(3-Butenyloxy)-2,3-difluoro-4'-(5,5,6,6,7,7,8,8,8-nonafluorooctyloxy)biphenyl

Quantities: diethyl azodicarboxylate (0.26 g, 1.5 mmol), 3-buten-1-ol (0.15 g, 2.1 mmol), 2,3-difluoro-4-hydroxy-4'-(5,5,6,6,7,7,8,8,8-nonafluorooctyloxy)biphenyl (Preparation 7, 0.7 g, 1.4 mmol) and triphenylphosphine (0.39 g, 1.5 mmol). The experimental procedure was described previously in Preparation 3A Yield=0.7 g (88%); Mesomorphism (T/° C.): Cryst 48 S$_A$ 81.2 Iso.

$\delta_H$ (270 MHz; CDCl$_3$; Me$_4$Si): 1.88 (4H, m, C$_2$H$_4$), 2.17 (2H, m, CF$_2$CH$_2$), 2.60 (2H, qt, J 6.8 and 1.3, CH$_2$—CH=CH$_2$), 4.05 (2H, t, J 5.7, OCH$_2$Rf), 4.13 (2H, t, J 6.8, OCH$_2$), 5.15 (1H, ddt, J 10.5, 1.7 and 1.3, ZCH=CH$_2$), 5.20 (1H, ddt, J 17.2, 1.7 and 1.3, ECH=CH$_2$), 5.93 (1H, ddt, J 17.2, 10.5 and 6.8, CH=CH$_2$), 6.79 (1H, ABXY, OC$_6$H$_2$F$_2$), 6.96 (2H, AA'BB', OC$_6$H$_4$), 7.06 (1H, ABXY, C$_6$F$_2$H$_2$), 7.43 (2H, AA'BB', C$_6$H$_4$). $\nu_{max}$(KBr disc)/cm$^{-1}$: 3074 (=C—H str), 2944 (—CH$_2$—, C—H asym str), 2872 (—CH$_2$—, C—H sym str), 1627, 1603 and 1500 (C=C str), 1463 (—CH$_2$— sci, C—H def), 1218 (C—F and aryl-O str), 1129 and 1078 (C—O str), 800 (C—H o.o.p.d.). m/z: 550 [M]$^+$, 497.

EXAMPLE 1

2-Difluoro-4-nonyl-4'-(5,5,6,6,7,7,8,8,8-nonafluorooctyloxy)biphenyl (Compound 12 in Table 2)

Quantities: 4-bromo-1-(5,5,6,6,7,7,8,8,8-nonafluorooctyloxy)benzene (Preparation 5, 1.34 g, 3.0 mmol), 2,3-difluoro-4-nonylphenylboronic acid (0.94 g, 3.3 mmol), tetrakis(triphenylphosphine)palladium(0) (104 mg, 90 µmol) and aqueous sodium carbonate (2 mol cm$^3$, 3 cm$^3$). The experimental procedure was described previously for in Preparation 5 except for the further purification by recrystallisation from hexane (HPLC standard).

Yield=0.7 g (39%); Purity (HPLC): 100.0%; Element Analysis: Calc. (found) for $C_{29}H_{33}F_{11}O$ (606.56): C, 57.43 (57.37); H, 5.48 (5.47) %. Mesomorphism (T/° C.): Cryst 47 $S_A$ 54.6 Iso.

$\delta_H$ (270 MHz; CDCl$_3$; Me$_4$Si): 0.88 (3H, t, J 6.7, CH$_3$), 1.27 (12H, m, C$_6$H$_{12}$), 1.63 (2H, m, PhCH$_2$CH$_2$), 1.89 (4H, m, C$_2$H$_4$), 2.18 (2H, m, CF$_2$CH$_2$), 2.67 (2H, t, J 7.5, PhCH$_2$), 4.05 (2H, t, J 5.7, OCH$_2$), 6.95 (1H, ABXY, OC$_6$F$_2$H$_2$), 6.97 (2H, AA'BB', OC$_6$H$_4$), 7.07 (1H, ABXY, C$_6$F$_2$H$_2$), 7.47 (2H, AA'BB', C$_6$H$_4$). $\nu_{max}$(KBr disc)/cm$^{-1}$: 2954 (CH$_3$—, C—H asym str), 2922 (—CH$_2$—, C—H asym str), 2850 (CH$_3$—, —CH$_2$—, C—H sym str), 1608, 1520 and 1487 (C═C str), 1454 (CH$_3$— asym, —CH$_2$— sci, C—H def), 1250 and 1215 (C—F and aryl-O str), 1179 (C—O str), 893, 821 (C—H o.o.p.d.), 718. m/z: 606 [M]$^+$, 506, 493, 332, 219.

EXAMPLE 2

2,3-Difluoro-4-octyloxy-4'-(5,5,6,6,7,7,8,8,8-nonafluorooctyloxy)biphenyl (Compound 9 in Table 2)

Quantities: 2',3'-difluoro-4'-octyloxy-4-hydroxybiphenyl (Preparation 12, 1.0 g, 3 mmol), 5,5,6,6,7,7,8,8,8-nonafluorooctan-1-ol (Preparation 2A, 0.88 g, 3 mmol), diethyl azodicarboxylate (0.52 g, 3 mmol) and triphenylphosphine (0.79 g, 3 mmol). The experimental procedure was described previously in Preparation 3, except for the further purification by recrystallisation from hexane (HPLC standard).

Yield=1.4 g (77%); Purity (HPLC): 100.0%; Element Analysis: Calc. (found) for $C_{28}H_{31}F_{11}O_2$ (608.54): C, 55.27 (55.17); H, 5.13 (4.98) %. Mesomorphism (T/° C.): Cryst 47 $S_A$ 82.9. Iso.

$\delta_H$ (270 MHz; CDCl$_3$; Me$_4$Si): 0.89 (3H, t, J 6.8, CH$_3$), 1.31 (8H, m, C$_4$H$_8$), 1.48 (2H, m, OCH$_2$CH$_2$CH$_2$), 1.86 (6H, m, OCH$_2$CH$_2$, C$_2$H$_4$), 2.18 (2H, m, CF$_2$CH$_2$), 4.04 (2H, t, J 6.0, OCH$_2$), 4:06 (2H, t, J 6.6, OCH$_2$), 6.77 (1H, ABXY, OC$_6$F$_2$H$_2$), 6.96 (2H, AA'BB', OC$_6$H$_4$), 7.05 (1H, ABXY, C$_6$F$_2$H$_2$), 7.43 (2H, AA'BB', C$_6$H$_4$). $\nu_{max}$(KBr disc)/cm$^{-1}$: 2958 (CH$_3$—, C—H asym str), 2930 (—CH$_2$—, C—H asym str), 2878 (CH$_3$—, C—H sym str), 2854 (—CH$_2$—, C—H sym str), 1630, 1608 and 1504 (C═C str), 1467 (CH$_3$— asym, —CH$_2$— sci, C—H def), 1220 (C—F and aryl-O str), 1132 and 1082 (C—O str), 882, 839 and 800 (C—H o.o.p.d.), 725. m/z: 539 [M-69, —CF$_3$]$^+$, 496, 348, 335, 223.

EXAMPLE 3

2,3-Difluoro-4-(5,5,6,6,7,7,8,8,8-nonafluorooctyloxy)-4'-octyloxybiphenyl (Compound 11 in Table 2)

Quantities: 4-iodo-1-octyloxybenzene (0.83 g, 2.5 mmol), 2,3-difluoro-4-(5,5,6,6,7,7,8,8,8-nonafluorooctyloxy) phenylboronic acid (Preparation 4, 1.34 g, 3 mmol), tetrakis(triphenylphosphine)palladium(0) (86.8 mg, 75 µmol) and aqueous sodium carbonate (2 mol cm$^{-3}$, 2.5 cm$^3$). The experimental procedure was described previously in Example 1.

Yield=1.0 g (66%); Purity (HPLC): 100.0%; Element Analysis: Calc. (found) for $C_{28}H_{31}F_{11}O_2$ (608.54): C, 55.27 (55.31); H, 5.13 (5.13) %. Mesomorphism (T/° C.): Cryst 83 $S_A$ 90.8 Iso. $\delta_H$ (270 MHz; CDCl$_3$; Me$_4$Si): 0.89 (3H, t, J 6.8, CH$_3$), 1.31 (8H, m, C$_4$H$_8$), 1.47 (2H, m, OCH$_2$CH$_2$CH$_2$), 1.80 (2H, m, OCH$_2$CH$_2$), 1.90 (4H, m, C$_2$H$_4$), 2.20 (2H, m, CF$_2$CH$_2$), 3.99 (2H, t, J 6.5, OCH$_2$), 4.11 (2H, t, J 5.7, OCH$_2$), 6.77 (1H, ABXY, OC$_6$F$_2$H$_2$), 6.96 (2H, AA'BB', OC$_6$H$_4$), 7.06 (1H, ABXY, C$_6$F$_2$H$_2$), 7.41 (2H, AA'BB', C$_6$H$_4$). $\nu_{max}$(KBr disc)/cm$^{-1}$: 2956 (CH$_3$—, C—H asym str), 2924 (—CH$_2$—, C—H asym str), 2874 (CH$_3$—, C—H sym str), 2852 (—CH$_2$—, C—H sym str), 1628, 1606 and 1502 (C═C str), 1464 (CH$_3$— asym, —CH$_2$— sci, C—H def), 1219 (C—F and aryl-O str), 1131 and 1081 (C—O str), 881, 840 and 798 (C—H o.o.p.d.), 717. m/z: 608 [M]$^+$, 591, 496, 477.

EXAMPLE 4

2,3-Difluoro-4-(5,5,6,6,7,7,8,8 8nonafluorooctyloxy)-4'-nonylbiphenyl (Compound 13 in Table 2)

Quantities: 4-bromo-1-nonylbenzene (0.71 g, 2.5 mmol), 2,3-difluoro-4-(5,5,6,6,7,7,8,8,8-nonafluorooctyloxy) phenylboronic acid (Preparation 4, 1.34 g, 3 mmol), tetrakis(triphenylphosphine)palladium(0) (86.8 mg, 75 µmol) and aqueous sodium carbonate (2 mol cm$^{-3}$, 2.5 cm$^3$). The experimental procedure was described previously in Example 1.

Yield=1.0 g (66%); Purity (HPLC): 100.0%; Element Analysis: Calc. (found) for $C_{29}H_{33}F_{11}O$ (606.56): C, 57.43 (57.25); H, 5.48 (5.37) %. Mesomorphism (T/° C.): Cryst 50 $S_A$ 60.2 Iso. $\delta_H$ (270 MHz; CDCl$_3$; Me$_4$Si): 0.88 (3H, t, J 6.7, CH$_3$), 1.27 (12H, m, C$_6$H$_{12}$), 1.64 (2H, m, PhCH$_2$CH$_2$), 1.91 (4H, m, C$_2$H$_4$), 2.20 (2H, m, CF$_2$CH$_2$), 2.64 (2H, t, J 7.7, PhCH$_2$), 4.12 (2H, t, J 5.7, OCH$_2$), 6.78 (1H, ABXY, OC$_6$F$_2$H$_2$), 7.10 (1H, ABXY, C$_6$F$_2$H$_2$), 7.25 (2H, AA'BB', OC$_6$H$_4$), 7.41 (2H, AA'BB', C$_6$H$_4$). $\nu_{max}$(KBr disc)/cm$^{-1}$: 2956 (CH$_3$—, C—H asym str), 2924 (—CH$_2$—, C—H asym str), 2884 (CH$_3$—, C—H sym str), 2854 (—CH$_2$—, C—H sym str), 1633 and 1503 (C═C str), 1470 (CH$_3$— asym, —CH$_2$— sci, C—H def), 1239 and 1214 (C—F and aryl-O str), 1132 and 1079 (C—O str), 850 (C—H o.o.p.d.), 769. m/z: 606 [M]$^+$, 506, 493, 332, 219.

EXAMPLE 5

2,3-Difluoro-4-(5,5,6,6,7,7,8,8,8-nonafluorooctyloxy)-4'-5,6,6,7,7,8,8,8-nonafluorooctyloxy)biphenyl (Compound 10 in Table 2)

Quantities: 4-bromo-1-(5,5,6,6,7,7,8,8,8-nonafluorooctyloxy)benzene (Preparation 3A, 1.12 g, 2.5 mmol), 2,3-difluoro-4-(5,5,6,6,7,7,8,8,8-nonafluorooctyloxy) phenylboronic acid (Preparation 4, 1.34 g, 3 mmol), tetrakis(triphenylphosphine)palladium(0) (86.8 mg, 75 µmol) and aqueous sodium carbonate (2 mol cm$^{-3}$, 2.5 cm$^3$). The experimental procedure was described previously in Example 1.

Yield=1.7 g (88%); Purity (HPLC): 100.0%; Element Analysis: Calc. (found) for $C_{28}H_{22}F_{20}O_2$ (770.45): C, 43.65 (43.62); H, 2.88 (2.64) %. Mesomorphism (T/° C.): Cryst 74

$S_A$ 82.0 Iso. $\delta_H$ (270 MHz; CDCl$_3$; Me$_4$Si): 1.89 (8H, m, 2×C$_2$H$_4$), 2.18 (4H, m, 2×CF$_2$CH$_2$), 4.05 (2H, t, J 5.7, OCH$_2$), 4.12 (2H, t, J 5.7, OCH$_2$), 6.78 (1H, ABXY, OC$_6$F$_2$H$_2$), 6.96 (2H, AA'BB', OC$_6$H$_4$), 7.07 (1H, ABXY, C$_6$F$_2$H$_2$), 7.43 (2H, AA'BB', C$_6$H$_4$). $\nu_{max}$(KBr disc)/cm$^{-1}$: 2958 (CH$_3$—, C—H asym str), 2930 (—CH$_2$—, C—H asym str), 2878 (CH$_3$—, C—H sym str), 2854 (—CH$_2$—, C—H sym str), 1627, 1605 and 1502 (C=C str), 1475 (—CH$_2$— sci, C—H def), 1244 (C—F and aryl-O str), 1131 and 1078 (C—O str), 849 (C—H o.o.p.d), 721. m/z: 601 [M-169, —C$_3$F$_7$]$^+$, 509, 496, 316, 222.

COMPARATIVE EXAMPLE 1

2,3-Difluoro-4-octyloxy-4'-octyloxybiphenyl

Quantities: 4-iodo-1-octyloxybenzene (0.83 g, 2.5 mmol), 2,3-fluoro-4-octyloxyphenylboronic acid (1.34 g, 3 mmol), tetrakis(triphenylphosphine)palladium(0) (86.8 mg, 75 µmol) and aqueous sodium carbonate (2 mol cm$^{-3}$, 2.5 cm$^3$). The experimental procedure was described previously in Example 1.

Yield=0.6 g (54%); Purity (HPLC): 100.0%; Element Analysis: Calc. (found) for C$_{28}$H$_{40}$F$_2$O$_2$ (446.62): C, 75.30 (75.30); H, 9.03 (9.04) %. Mesomorphism (T/° C.): Cryst 57 S$_C$ 59.5 S$_A$ 60.1 N 63.7 Iso. $\delta_H$ (270 MHz; CDCl$_3$; Me$_4$Si): 0.89 (6H, t, J 6.6, 2×CH$_3$), 1.31 (16H, m, 2×C$_4$H$_8$), 1.47 (4H, m, 2×OCH$_2$CH$_2$CH$_2$), 1.84 (4H, m, 2×OCH$_2$CH$_2$), 3.99 (2H, t, J 6.5, PhOCH$_2$), 4.06 (2H, t, J 6.6, C$_6$F$_2$H$_2$OCH$_2$), 6.77 (1H, ABXY, OC$_6$F$_2$H$_2$), 6.96 (2H, AA'BB', OC$_6$H$_4$), 7.05 (1H, ABXY, C$_6$F$_2$H$_2$), 7.41 (2H, AA'BB', C$_6$H$_4$). $\nu_{max}$(KBr disc)/cm$^{-1}$: 2954 (CH$_3$—, C—H asym str), 2920 (—CH$_2$—, C—H asym str), 2870 (CH$_3$—, C—H sym str), 2850 (—CH$_2$—, C—H sym str), 1631, 1606 and 1502 (C=C str), 1464 (CH$_3$— asym, —CH$_2$— sci, C—H def), 1300, 1272, 1251 (aryl-O str), 1076 (C—O str), 838 and 798 (C—H o.o.p.d.). m/z: 446 [M]$^+$, 334, 222.

EXAMPLE 6

2,3-Difluoro-4"-(5,5,6,6,7,7,8,8,8-nonafluoroocty-loxy)-4-octyloxy-1,1':4',1"-terphenyl (Compound No. 3 in Table 1)

Quantities: 4-bromo-4'-(5,5,6,6,7,7,8,8,8-nonafluoroocty-loxy)biphenyl (Preparation 3B, 1.57 g, 3.0 mmol), 2,3-difluoro-4-octyloxyphenylboronic acid (0.90 g, 3.1 mmol), tetrakis(triphenylphosphine)palladium(0) (104 mg, 90 µmol) and aqueous sodium carbonate (2 mol cm$^{-3}$, 3 cm$^3$). The experimental procedure was described previously in Example 1.

Yield=0.8 g (39%); Purity (HPLC): 98.27%; Element Analysis: Calc. (found) for C$_{34}$H$_{35}$F$_{11}$O$_2$ (684.63): C, 59.65 (59.30); H, 5.15 (5.10) %. Mesomorphism (T/° C.): Cryst 99 S$_C$ 184.7 S$_A$ 206.8 Iso. $\delta_H$ (270 MHz; CDCl$_3$; Me$_4$Si): 0.90 (3H, t, J 6.7, CH$_3$), 1.32 (8H, m, C$_4$H$_8$), 1.49 (2H, m, OCH$_2$CH$_2$CH$_2$), 1.85 (2H, m, OCH$_2$CH$_2$), 1.89 (4H, m, C$_2$H$_4$), 2.18 (2H m, CF$_2$CH$_2$), 4.02 (2H, t, J 6.5, OCH$_2$), 4.08 (2H, t, J 6.5, OCH$_2$), 6.81 (1H. ABXY, OC$_6$F$_2$H$_2$), 6.98 (2H, AA'BB', OC$_6$H$_4$), 7.14 (1H, ABXY, C$_6$F$_2$H$_2$), 7.57 (4H, AA'BB', C$_6$H$_4$), 7.63 (2H, AA'BB', C$_6$H$_4$). $\nu_{max}$(KBr disc)/cm$^{-1}$: 2956 (CH$_3$—, C—H asym str), 2928 (—CH$_2$—, C—H asym str), 2874 (CH$_3$—, C—H sym str), 2854 (—CH$_2$—, C—H sym str), 1627, 1604 and 1496 (C=C str), 1464 (CH$_3$-asym, —CH$_2$— sci, C—H def), 1300, 1217 (C—F and aryl-O str), 1130 and 1075 (C—O str), 802 (C—H o.o.p.d.), 720. m/z: 572 [M-112, —C$_8$H$_{16}$]$^+$, 409, 298.

EXAMPLE 7

2,3-Difluoro-4-(5,5,6,6,7,7,8,8,8-nonafluoroocty-loxy)-4"-octyloxy-1,1':4',1"-terphenyl (Compound No 1 in Table 1)

Quantities: 4-bromo-4'-octyloxybiphenyl (1.08 g, 3.0 mmol), 2,3-difluoro-4-(5,5,6,6,7,7,8,8,8-nonafluoroocty-loxy)phenylboronic acid (Preparation 4, 1.68 g, 3.75 mmol), tetrakis(triphenylphosphine)palladium(0) (104 mg, 90 µmol) and aqueous sodium carbonate (2 mol cm$^{-3}$, 0 cm$^3$). The experimental procedure was described previously in Example 1.

Yield=0.25 g (12%); Purity (HPLC): 100.0%; Element Analysis: Calc. (found) for C$_{34}$H$_{35}$F$_{11}$O$_2$ (684.63): C, 59.65 (59.89); H, 5.15 (5.20) %. Mesomorphism (T/° C.): Cryst 127 S$_C$ 183.8 S$_A$ 216.1 Iso.

$\delta_H$ (270 MH; CDCl$_3$; Me$_4$Si): 0.90 (3H, t, J 6.7, CH$_3$), 1.31 (8H, m, C$_4$H$_8$), 1.48 (2H, m, OCH$_2$CH$_2$CH$_2$), 1.81 (2H, m, OCH$_2$CH$_2$), 1.94 (4H, m, C$_2$H$_4$), 2.21 (2H, m, CF$_2$CH$_2$), 4.01 (2H, t, J 6.5, OCH$_2$), 4.14 (2H, t, J 5.7, OCH$_2$), 6.81 (1H, ABXY, OC$_6$F$_2$H$_2$), 6.99 (2H, AA'BB', OC$_6$H$_4$), 7.15 (1H, ABXY, C$_6$F$_2$H$_2$), 7.56 (4H, AA'BB', C$_6$H$_4$), 7.63 (2H, AA'BB', C$_6$H$_4$). $\nu_{max}$(KBr disc)/cm$^{-1}$: 2956 (CH$_3$—, C—H asym str), 2922 (—CH$_2$—, C—H asym str), 2876 (CH$_3$—, C—H sym str), 2856 (—CH$_2$—, C—H sym str), 1627, 1604 and 1495 (C=C str), 1465 (CH$_3$— asym, —CH$_2$— sci, C—H def), 1300, 1260 and 1218 (C—F and aryl-O str), 1130 and 1081 (C—O str), 881, 800 (C—H o.o.p.d.). m/z: 572 [M-112, —C$_8$H$_{16}$]$^+$, 466, 409, 298.

EXAMPLE 8

2',3'-Difluoro-4-(5,5,6,6,7,7,8,8,8-nonafluoroocty-loxy)-4"-octyloxy-1,1':4',1"-terphenyl (Compound 2 in Table 1)

Quantities: 2',3'-difluoro-4"-octyloxy-4-hydroxy-1,1':4', 1"-terphenyl (0.5 g, 1.2 mmol), 5,5,6,6,7,7,8,8,8-nonafluorooctan-1-ol (Preparation 2A, 0.36 g, 1.2 mmol), diethyl azodicarboxylate (0.21 g, 1.2 mmol) and triphenylphosphine (0.32 g, 1.2 mmol). The experimental procedure was described previously in Example 2.

Yield=0.6 g (73%); Purity (HPLC): 100.0%; Element Analysis: Calc. (found) for C$_{34}$H$_{35}$F$_{11}$O$_2$ (684.63): C, 59.65 (59.77); H, 5.15 (5.13)%. Mesomorphism (T/° C.): Cryst 83 S$_C$ 155.7 S$_A$ 193.2 Iso.

$\delta_H$ (270 MHz; CDCl$_3$; Me$_4$Si): 0.90 (3H, t, J 6.7, CH$_3$), 1.30 (8H, m, C$_4$H$_8$), 1.48 (2H, m, OCH$_2$CH$_2$CH$_2$), 1.82 (2H, n, OCH$_2$CH$_2$), 1.90 (4H, m, C$_2$H$_4$), 2.19 (2H, m, CF$_2$CH$_2$), 4.01 (2H, t, J 6.7, OCH$_2$), 4.06 (2H, t, J 5.8, OCH$_2$), 6.99 (4H, AA'BB', OC$_6$H$_4$), 7.21 (2H, ABXY, C$_6$F$_2$H$_2$), 7.52 (4H, AA'BB', C$_6$H$_4$). $\nu_{max}$(KBr disc)/cm$^{-1}$: 2954 (CH$_3$—, C—H asym str), 2922 (—CH$_2$—, C—H asym str), 2872 (CH$_3$—, C—H sym str), 2854 (—CH$_2$—, C—H sym str), 1606, 1522 and 1481 (C=C str), 1453 (—CH$_2$— sci C—H def), 1247 and 1215 (C—F and aryl-O str), 1130 (C—O str), 810 (C—H o.o.p.d.). m/z: 684 [M]$^+$, 572, 298.

EXAMPLE 9

2',3'-Difluoro-4-(5,5,6,6,7,7,8,8,8-nonafluoroocty-loxy)-4"-nonyl-1,1':4',1"-terphenyl (Compound 4 in Table 1)

Quantities: 2',3'-difluoro-4"-nonyl-4-hydroxy-1,1':4',1"-terphenyl (0.4 g, 1.0 mmol), 5,5,6,6,7,7,8,8,8-nonafluorooctan-1-ol (Preparation 2A, 0.29 g, 1.0 mmol), diethyl azodicarboxylate (0.17 g, 1.0 mmol) and triphenylphosphine (0.26 g, 1.0 mmol). The experimental procedure was described previously in Example 2.

Yield=0.5 g (73%); Purity (HPLC): 100.0%; Element Analysis: Calc. (found) for $C_{35}H_{37}F_{11}O$ (682.66): C, 61.58 (61.58); H, 5.46 (5.46) %. Mesomorphism (T/° C.): Cryst 76 $S_C$ 116.4 $S_A$ 163.6 Iso.

$\delta_H$ (270 MHz; CDCl$_3$; Me$_4$Si): 0.89 (3H, t, J 6.7, CH$_3$), 1.28 (12H, m, $C_6H_{12}$), 1.66 (2H, m, PhCH$_2$CH$_2$), 1.90 (4H, m, $C_2H_4$), 2.19 (2H, m, CF$_2$CH$_2$), 2.66 (2H, t, J 7.7, PhCH$_2$), 4.06 (2H, t, J 5.7, OCH$_2$), 6.99 (2H, AA'BB', OC$_6$H$_4$), 7.22 (2H, ABXY, $C_6F_2H_2$), 7.29 (2H, AA'BB', $C_6H_4$), 7.50 (2H, AA'BB', $C_6H_4$), 7.53 (2H, AA'BB', $C_6H_4$). $\nu_{max}$(KBr disc)/cm$^{-1}$: 2954 (CH$_3$—, C—H asym str), 2920 (—CH$_2$—, C—H asym str), 2874 (CH$_3$—, C—H sym str), 2848 (—CH$_2$—, C—H sym str), 1608, 1522 and 1481 (C=C str), 1452 (—CH$_2$— sci, C—H def), 1216 (C—F and aryl-O str), 1131 (C—O str), 816 (C—H o.o.p.d.), 718. m/z: 682 [M]$^+$, 665, 582, 569, 295.

EXAMPLE 10

2-[2,3-Difluoro-4-(5,5,6,6,7,7,8,8,8-nonafluorooctyloxy)biphenyl-4'yl]-5-nonyl-1,3-dioxane (Compound no 22 in Table 3)

Quantities: 2-(4-bromophenyl)-5-nonyl-1,3-dioxane (0.92 g, 2.5 mmol), 2,3-difluoro-4-(5,5,6,6,7,7,8,8,8-nonafluorooctyloxy)phenylboronic acid (Preparation 4, 1.34 g, 3 mmol), tetrakis(triphenylphosphine)palladium(0) (86.8 mg, 75 μmol) and aqueous sodium carbonate (2 mol cm$^{-3}$, 2.5 cm$^3$). The experimental procedure was described previously in Example 1.

Yield=1.25 g (72%); Purity (HPLC): 100.0%; Element Analysis: Calc. (found) for $C_{34}H_{35}F_{11}O_2$ (692.65): C, 57.22 (57.36); H, 5.68 (5.53) %. Mesomorphism (T/° C.): Cryst 78 $S_A$ 164.0 Iso.

$\delta_H$ (270 MHz; CDCl$_3$; Me$_4$Si): 0.89 (3H, t, J 6.7, CH$_3$), 1.11 (2H, m, CH$_3$CH$_2$), 1.28 (14H, m, $C_7H_{14}$), 1.90 (4H, m, $C_2H_4$), 2.17 (3H, m, CF$_2$CH$_2$, 5-H), 3.55 (2H, dd, J 11.5 and 11.5, Ha), 4.12 (2H, t, J 6.5, OCH$_2$), 4.25 (2H, dd, J 11.5 and 4.5, He), 5.46 (1H, s, 2-H), 6.78 (1H, ABXY, OC$_6$H$_2$F$_2$), 7.08 (1H, ABXY, $C_6H_2F_2$), 7.50 (2H, AA'BB', $C_6H_4$), 7.52 (2H, AA'BB', $C_6H_4$). $\nu_{max}$(KBr disc)/cm$^{-1}$: 2952 (CH$_3$—, C—H asym str), 2918 (—CH$_2$—, C—H asym str), 2844 (CH$_3$—, —CH$_2$—, C—H sym str), 1625 and 1502 (C=C str), 1464 (CH$_3$— asym, —CH$_2$— sci, C—H def), 1385 (CH$_3$—, C—H sym def), 1315, 1299, 1232 and 1218 (C—F and aryl-O str), 1128, 1077 and 1020 (alkyl-O str), 797 (C—H o.o.p.i), 717. m/z: 508 [M-184, —OC$_{12}$H$_{24}$]$^+$, 493, 480, 417, 234.

EXAMPLE 11

(2S,3S)-2,3-Difluoro-4-(5,5,6,6,7,7,8,8,8-nonafluorooctyloxy)biphenyl-4'-yl 2-chloro-3-methylpentanoate (Compound 18 in Table 2)

A solution of (2S,3S)-(−)-(-2-chloro-3-methylpentanoic acid (0.23 g, 1.5 mmol), 2,3-difluoro-4-(5,5,6,6,7,7,8,8,8-nonafluorooctyloxy)-4'-hydroxybiphenyl (Preparation 9, 0.5 g, 1 mmol), N,N'-dicyclohexylcarbodiimide (0.23 g, 1.1 mmol) and 4-(N,N-dimethylamino)pyridine (0.01 g, 0.1 mmol) in dichloromethane (10 cm$^3$) was stirred overnight at room temperature. The reaction mixture was filtered and the filtrate washed with water (2×25 cm$^3$) and dried (MgSO$_4$). The solvent was removed in vacuo, the product purified by flash column chromatography (light petroleum /dichloromethane) and recrystallisation from hexane (HPLC standard).

Yield=0.45 g (72%); Purity (HPLC): 100.0%; Element Analysis: Calc. (found) for $C_{26}H_{24}ClF_{11}O_3$ (628.91): C, 49.66 (49.71); H, 3.85 (3.76) %; $[\alpha]_D^{21°}$=−0.00 (13.39 g/dm$^3$ in CHCl$_3$). Mesomorphism (T/° C.): Cryst 48 $S_A$ 53.2 Iso.

$\delta_H$(270 MHz; CDCl$_3$; Me$_4$Si): 1.00 (3H, t, J 7.5, CH$_3$), 1.15 [3H, d, J 7.0, CH(CH$_3$)], 1.43 [1H, m, CH$_2$CH(CH$_3$)], 1.78 [1H, m, CH$_2$CH(CH$_3$)], 1.93 (4H, m, $C_2H_4$), 2.20 (2H, m, CF$_2$CH$_2$), 2.23 [1H, m, CH(CH$_3$)], 4.13 (2H, t, J 5.7, OCH$_2$), 4.40 [1H, d, J 7.1, CHCl], 6.80 (1H, ABXY, OC$_6$F$_2$H$_2$), 7.09 (1H, ABXY, $C_6F_2H_2$), 7.20 (2H, AA'BB', CO$_2$C$_6$H$_4$), 7.53 (2H, AA'BB', $C_6H_4$). $\nu_{max}$(KBr disc)/cm$^{-1}$: 2964 (CH$_3$—, C—H asym str), 2936 (—CH$_2$—, C—H asym str), 2878 (CH$_3$—, —CH$_2$—, C—H sym str), 1754 (C=O str), 1627 and 1496 (C=C str), 1465 (CH$_3$— asym, —CH$_2$— sci, C—H def), 1228 and 1216 (C—F and aryl-O str), 1129 and 1076 (C—O str), 848 (C—H o.o.p.d.). m/z: 629 [M+1]$^+$, 497, 367, 355, 222.

EXAMPLE 12

(2S,3S)-2,3-Difluoro-4'-(5,5,6,6,7,7,8,8,8nonafluorooctyloxy)biphenyl-4-yl 2-chloro-3-methylpentanoate (Compound 19 in Table 2)

Quantities: (2S,3S)-(−)-2-chloro-3-methylpentanoic acid (0.23 g, 1.5 mmol), 2,3-difluoro-4'-(5,5,6,6,7,7,8,8,8-nonafluorooctyloxy)-4-hydroxybiphenyl (Preparation 7, 0.5 g, 1 mmol), N,N'-dicyclohexylcarbodiimide (0.23 g, 1.1 mmol) and 4-N,N-dimethylamino)pyridine (0.01 g, 0.1 mmol). The experimental procedure was described previously in Example 11.

Yield=0.4 g (64%); Purity (HPLC): 100.0%; Element Analysis: Calc. (found) for $C_{26}H_{24}ClF_{11}O_3$ (628.91): C, 49.66 (49.76); H, 3.85 (3.76) %; $[\alpha]_D^{22°}$=+3.30 (21.69 g/dm$^3$ in CHCl$_3$). Mesomorphism (T/° C.): Cryst 48 $S_A$ 53.2 Iso.

$\delta_H$ (270 MHz; CDCl$_3$; Me$_4$Si): 1.00 (3H, t, J 7.5, CH$_3$), 1.16 [3H, d, J 7.0, CH(CH$_3$)], 1.43 [1H, m, CH$_2$CH(CH$_3$)], 1.78 [1H, m, CH$_2$CH(CH$_3$)], 1.89 (4H, m, $C_2H_4$), 2.18 (2H, m, CF$_2$CH$_2$), 2.25 [1H, m, CH(CH$_3$)], 4.05 (2H, t, J 5.7, OCH$_2$), 4.46 [1H, d, J 7.0, CHCl], 6.98 (2H, AA'BB', OC$_6$H$_4$), 7.00 (1H, ABXY, CO$_2$C$_6$F$_2$H$_2$), 7.18 (1H, ABXY, $C_6F_2H_2$), 7.46 (2H, AA'BB', $C_6H_4$). $\nu_{max}$(KBr disc)/cm$^{-1}$: 2966 (CH$_3$—, C—H asym str), 2936 (—CH$_2$—, C—H asym str), 2878 (CH$_3$—, —CH$_2$—, C—H sym str), 1779 (C=O str), 1604, 1515 and 1491 (C=C str), 1467 (CH$_3$— asym, —CH$_2$— sci, C—H def), 1242 (C—F and aryl-O str), 1132 (C—O str), 827 (C—H o.o.p.d), 770. m/z: 572 [M-56, —C$_4$H$_8$]$^+$, 496, 222.

EXAMPLE 13

(S)-Non-3-yl 4'-(12,12,13,13,14,14,15,15,15-Nonafluoropentadecyloxy)biphenyl-4-carboxylate (Compound 20 in Table 2)

Quantities: diethyl azodicarboxylate (0.09 g, 0.5 mmol), (S)-non-3-yl 4'-hydroxybiphenyl-4-carboxylate (0.17 g, 0.5 mmol), 12,12,13,13,14,14,15,15,15-nonafluoropentadecan-1-ol (0.21 g, 0.5 mmol) and triphenylphosphine (0.13 g, 0.5 mmol). The experimental procedure was described previously in Preparation 3A.

Yield=0.08 g (22%); mp. 43-45° C.; Purity (HPLC): 100.0%; $[\alpha]_D^{28°}$=+10.40° (18.49 g/dm$^3$ in CHCl$_3$).

$\delta_H$ (270 MHz; CDCl$_3$; Me$_4$Si): 0.87 (3H, t, J 6.8, CH$_3$), 0.96 (3H, t, J 7.5, CH$_3$), 1.26 (8H, m, C$_4$H$_8$), 1.32 (14H, m, C$_7$H$_{14}$), 1.63 (2H, m, CF$_2$CH$_2$CH$_2$), 1.69 [4H, m, CH(CH$_2$)$_2$], 1.81 (2H, qn, J 7.5, OCH$_2$CH$_2$), 2.05 (2H, m, CF$_2$CH$_2$), 4.01 (2H, t, J 6.6, OCH$_2$), 5.09 (1H, qn J 6.2, OCH), 6.99 (2H, AA'BB', OC$_6$H$_4$), 7.56 (2H, AA'BB', C$_6$H$_4$), 7.62 (2H, AA'BB', C$_6$H$_4$), 8.09 (2H, AA'BB', C$_6$H$_4$CO$_2$). $\nu_{max}$(KBr disc)/cm$^{-1}$: 2920 (CH$_3$—, —CH$_2$—, C—H asym str), 2852 (CH$_3$—, —CH$_2$—, C—H sym str), 1697 (C=O str), 1607 and 1522 (C=C str), 1470 (CH$_3$— asym, —CH$_2$— sci C—H def), 1358, 1242 (C—F and aryl-O str), 1132 (C—O str), 835 (C—H o.o.p.d.), 774, 722. m/z: 627 [M-85, —C$_6$H$_{13}$]$^+$, 600.

EXAMPLE 14

2,3-Difluoro-4'-octyloxy-4-(4-pentamethyldisiloxybutyloxy)biphenyl (Compound 14 in Table 2)

A solution of pentamethyldisiloxane (0.3 g, 2 mmol) in dry toluene (10 cm$^3$) was added dropwise into a solution of 4-(3-butenyloxy)-2,3-difluoro-4'-octyloxybiphenyl (Preparation 14, 0.56 g, 1.4 mmol) and platinum divinyltetramethyldisiloxane complex (10 mm$^3$) in dry toluene (5 cm$^3$) under an atmosphere of dry nitrogen at room temperature. The reaction mixture was stirred for a further period of time at room temperature until HPLC analysis revealed a complete reaction (ca. 2-4 h). The solvent and the excess pentamethyldisiloxane were removed in vacuo, the product purified by flash column chromatography (light petroleum/dichloromethane) and recrystallisation from hexane (HPLC standard).

Yield=0.6 g (80%); mp. 26-28° C.; Purity PLC): 100.0%; Element Analysis: Calc. (found) for C$_{29}$H$_{46}$F$_2$O$_3$Si$_2$ (536.85): C, 64.88 (64.52); H, 8.64 (8.69) %.

$\delta_H$ (270 MHz; CD$_2$Cl$_2$; ExRef 5.30): 0.05 (15H, m, 5×SiCH$_3$), 0.58 (2H, t, J 8.5, SiCH$_2$), 0.87 (3H, t, J 6.7, CH$_3$), 1.28 (8H, m, C$_4$H$_8$), 1.50 (4H, m, 2×OCH$_2$CH$_2$CH$_2$), 1.80 (4H, m, 2×OCH$_2$CH$_2$), 3.97 (2H, t, J 6.5, OCH$_2$C$_7$H$_{15}$), 4.06 (2H, t, J 6.5, OCH$_2$), 6.80 (1H, ABXY, OC$_6$H$_2$F$_2$), 6.93 (2H, AA'BB', OC$_6$H$_4$), 7.06 (1H, ABXY, C$_6$F$_2$H$_2$), 7.39 (2H, AA'BB', C$_6$H$_4$). $\nu_{max}$(KBr disc)/cm$^{-1}$: 2948 (CH$_3$—, C—H asym str), 2924 (—CH$_2$—, C—H asym str), 2852 (CH$_3$—, —CH$_2$—, C—H sym str), 1624, 1606 and 1496 (C=C str), 1465 (CH$_3$— asym, —CH$_2$— sci C—H def), 1311, 1287 and 1248 (Si—C and aryl-O str), 1197, 1178, 1025 and 1003 (Si—O—Si, Si—O—C asym str and C—O str), 840 and 798 (Si—CH$_3$, Si—O—C def and C—H o.o.p.d.). m/z: 536 [M]$^+$, 504, 479, 464, 445, 424, 390, 368.

EXAMPLE 15

2,3-Difluoro-4-octyloxy-4'-(4-pentamethyldisiloxybutyloxy)biphenyl (Compound 15 in Table 2)

Quantities: pentamethyldisiloxane (0.24 g, 1.6 mmol) and 4'-(3-butenyloxy)-2,3-difluoro-4-octyloxybiphenyl (Preparation 16, 0.42 g, 1.1 mmol). The experimental procedure was described previously in Example 14.

Yield=0.2 g (34%/o); mp. 33.0-33.5° C.; Purity (HPLC): 100.0%; Element Analysis: Calc. (found) for C$_{29}$H$_{46}$F$_2$O$_3$Si$_2$ (536.85): C, 64.88 (64.98); H, 8.64 (8.68) %.

$\delta_H$ (270 MHz; CD$_2$Cl$_2$; ExRef 5.30): 0.05 (15H, m, 5×SiCH$_3$), 0.57 (2H, t, J 8.4, SiCH$_2$), 0.87 (3H, t, J 6.7, CH$_3$), 1.29 (8H, m, C$_4$H$_8$), 1.48 (4H, m, 2×OCH$_2$CH$_2$CH$_2$), 1.80 (4H, qn, J 7.0, 2×OCH$_2$CH$_2$), 3.98 (2H, t, J 6.5, OCH$_2$C$_7$H$_{15}$), 4.04 (2H, t, J 6.5, OCH$_2$), 6.79 (1H, ABXY, OC$_6$H$_2$F$_2$), 6.93 (2H, AA'BB', OC$_6$H$_4$), 7.06 (1H, ABXY, C$_6$F$_2$H$_2$), 7.39 (2H, AA'BB', C$_6$H$_4$). $\nu_{max}$(KBr disc)/cm$^{-1}$: 2950 (CH$_3$—, C—H asym str), 2922 (—CH$_2$—, C—H asym str), 2848 (CH$_3$—, —CH$_2$—, C—H sym str), 1627, 1604 and 1498 (C=C str), 1468 (CH$_3$— asym, —CH$_2$— sci, C—H def), 1288 and 1250 (Si—C and aryl-O str), 1067 (Si—O—Si, Si—O—C asym str and C—O str), 839 (Si—CH$_3$, Si—O—C def and C—H o.o.p.d.). m/z: 536 [M]$^+$, 521, 480, 465, 424, 381, 368, 353.

EXAMPLE 16

2,3-Difluoro-4"-octyloxy-4-(4-pentamethyldisiloxybutyloxy)-1,1':4',1"-terphenyl (Compound 5 in Table 1)

Quantities: pentamethyldisiloxane (0.1 g, 0.67 mmol) and 4-(3-butenyloxy)-2,3-difluoro-4"-octyloxy-1,1':4',1"-terphenyl (Preparation 17, 0.2 g, 0.43 mmol). The experimental procedure was described previously for in Example 14.

Yield=0.08 g (30%); Purity (HPLC): 100.0%; Element Analysis: Calc. (found) for C$_{35}$H$_{50}$F$_2$O$_3$Si$_2$ (612.95): C, 68.58 (68.52); H, 8.22 (8.35) %. Mesomorphism (T/° C.): Cryst 53 S$_C$ 137.8 Iso.

$\delta_H$ (270 MHz; CDCl$_3$; ExRef 7.26): 0.07 (15H, m, 5×SiCH$_3$), 0.59 (2H, t, J 7.2, SiCH$_2$), 0.90 (3H, t, J 6.8, CH$_3$), 1.30 (8H, m, C$_4$H$_8$), 1.51 (4H, m, 2×OCH$_2$CH$_2$CH$_2$), 1.82 (2H, m, OCH$_2$CH$_2$), 1.88 (2H, m, OCH$_2$CH$_2$), 4.01 (2H, t, J 6.5, OCH$_2$C$_7$H$_{15}$), 4.10 (2H, t, J 65, OCH$_2$), 6.82 (1H, ABXY, OC$_{61}$H$_2$F$_2$), 6.99 (2H, AA'BB', OC$_6$H$_4$), 7.14 (H, ABXY, C$_6$F$_2$H$_2$), 7.56 (4H, AA'BB', C$_6$H$_4$), 7.62 (2H, AA'BB', C$_6$H$_4$). $\nu_{max}$(KBr disc)/cm$^{-1}$: 2956 (CH$_3$—, C—H asym str), 2936 (—CH$_2$—, C—H asym str), 2860 (CH$_3$—, —CH$_2$—, C—H sym str), 1623, 1603 and 1494 (C=C str), 1464 (CH$_3$— asym, —CH$_2$— sci, C—H def), 1298 and 1250 (Si—C and aryl-O str), 1067 (Si—O—Si, Si—O—C asym str and C—O str), 843 and 829 (Si—CH$_3$, Si—O—C def and C—H o.o.p.d.). m/z: 613 [M+1]$^+$, 556, 541, 298.

EXAMPLE 17

2,3-Difluoro-4-octyloxy-4"-(4-pentamethyldisiloxybutyloxyy)1,1':4'1"-terphenyl (Compound 7 in Table 1)

Quantities: pentamethyldisiloxane (0.19 g, 1.3 mmol) and 4"-(3-butenyloxy)-2,3-difluoro-4-octyloxy-1,1':4',1"-terphenyl (Preparation 18, 0.4 g, 0.86 mmol). The experimental procedure was described previously in Example 14.

Yield=0.2 g (38%); Purity (HPLC): 100.0%; Element Analysis: Calc. (found) for C$_{35}$H$_{50}$F$_2$O$_3$Si$_2$ (612.95): C, 68.58 (68.59); H, 8.22 (8.45) %. Mesomorphism (T/° C.): Cryst 54 S$_C$ 119.6 Iso.

$\delta_H$ (270 MHz; CDCl$_3$; Me$_4$Si): 0.07 (15H, m, 5×SiCH$_3$), 0.59 (2H, t, J 8.4, SiCH$_2$), 0.89 (3H, t, J 6.6, CH$_3$), 1.30 (8H, m, C$_4$H$_8$), 1.53 (4H, m, 2×OCH$_2$CH$_2$CH$_2$), 1.84 (4H, m, 2×OCH$_2$CH$_2$), 4.02 (2H, t, J 6.5, OCH$_2$C$_7$H$_{15}$), 4.08 (2H, t, J 6.5, OCH$_2$), 6.81 (1H, ABXY, OC$_6$H$_2$F$_2$), 6.99 (2H, AA'BB', OC$_6$H$_4$), 7.13 (1H, ABXY, C$_6$F$_2$H$_2$), 7.56 (4H, AA'BB', C$_6$H$_4$), 7.62 (2H, AA'BB', C$_6$H$_4$). $\nu_{max}$(KBr disc)/cm$^{-1}$: 2952 (CH$_3$—, C—H asym str), 2924 (—CH$_2$—, C—H asym str), 2856 (CH$_3$—, —CH$_2$—, C—H sym str), 1633, 1604 and 1495 (C=C str), 1464 (CH$_3$— asym, —CH$_2$— sci C—H def), 1250 (Si—C and aryl-O str), 1179 and 1078 (Si—O—Si, Si—O—C asym str and C—O str), 841, 827 and 801 (Si—CH$_3$, Si—O—C def and C—H o.o.p.d.). m/z: 612 [M]$^+$, 597, 556, 541, 521, 500, 444.

EXAMPLE 18

2',3'-Difluoro-4-octyloxy-4"-(4-pentamethyldisiloxy-butyloxy)-1,1':4',1"-terphenyl (Compound 6 in Table 1)

Quantities: pentamethyldisiloxane (0.22 g, 1.5 mmol) and 4"-(3-butenyloxy)-2',3'-difluoro-4-octyloxy-1,1':4',1"-terphenyl (Preparation 19, 0.49 g, 1.05 mmol). The experimental procedure was described previously in Example 14.

Yield=0.5 g (78%); Purity (HPLC): 98.24%; Element Analysis: Calc. (found) for $C_{35}H_{50}F_2O_3Si_2$ (612.95): C, 68.58 (68.52); H, 8.22 (8.82) %. Mesomorphism (T/° C.): Cryst 70 $S_C$ 104.0 N 105.6 Iso.

$\delta_H$ (270 MH; $CD_2Cl_2$; ExRef 5.30): 0.06 (15H, m, 5×SiCH$_3$), 0.59 (2H , t, J 8.5, SiCH$_2$), 0.88 (3H, t, J 6.8, CH$_3$), 130 (8H, m, C$_4$H$_8$), 1.50 (4H, m, 2×OCH$_2$CH$_2$CH$_2$), 1.79 (2H, m, OCH$_2$CH$_2$), 1.81 (2H, m, OCH$_2$CH$_2$), 3.99 (2H, t, J 6.5, OCH$_2$C$_7$H$_{15}$), 4.01 (2H, t, J 6.5, OCH$_2$), 6.98 (4H, AA'BB', OC$_6$H$_4$), 7.22 (2H, ABXY, C$_6$F$_2$H$_2$), 7.50 (2H, AA'BB', C$_6$H$_4$). $v_{max}$(KBr disc)/cm$^{-1}$: 2952 (CH$_3$—, C—H asym str), 2922 (—CH$_2$—, C—H asym str), 2868 (CH$_3$—, C—H sym str), 2856 (—CH$_2$—, C—H sym str), 1604, 1520 and 1482 (C═C str), 1470 and 1453 (CH$_3$— asym, —CH$_2$— sci C—H def), 1290 and 1249 (Si—C and aryl-O str), 1179 and 1038 (Si—O—Si, Si—O—C asym str and C—O str), 847,832 and 810 (Si—CH$_3$, Si—O—C def and C—H o.o.p.d.). m/z: 612 [M]$^+$, 597, 556, 541, 500, 483, 298.

EXAMPLE 19

2',3'-Difluoro-4-nonyl-4"-(4-pentamethyldisiloxybu-tyloxy)-1,1':4',1"-terphenyl (Compound 8 in Table 1)

Quantities: pentamethyldisiloxane (0.22 g, 1.5 mmol) and 4"-(3-butenyloxy)-2',3'-difluoro-4-nonyl-1,1':4',1"-terphenyl (Preparation 20, 0.48 g, 1.04 mmol). The experimental procedure was described previously in Example 14.

Yield=0.4 g (63%); Purity (HPLC): 98.55%; Element Analysis: Calc. (found) for $C_{36}H_{52}F_2O_2Si_2$ (610.97): C, 70.77 (70.67); H, 8.58 (8.66) %. Mesomorphism (T/° C.): Cryst 28 $S_C$ 70.9 N 74.1 Iso.

$\delta_H$ (270 MHz; $CD_2Cl_2$; ExRef 5.30): 0.06 (15H, m, 5×SiCH$_3$), 0.59 (2H, t, J 8.5, SiCH$_2$), 0.87 (3H, t, J 7.0, CH$_3$), 1.27 (12H, m, C$_6$H$_{12}$), 1.50 (2H, m, OCH$_2$CH$_2$CH$_2$), 1.63 (2H, m, PhCH$_2$CH$_2$), 1.82 (2H, qn, J 7.0, OCH$_2$CH$_2$), 2.64 (2H, t, J 7.7, PhCH$_2$), 4.01 (2H, t, J 6.5, OCH$_2$), 6.98 (2H, AA'BB', OC$_6$H$_4$), 7.23 (2H, ABXY, C$_6$F$_2$H$_2$), 7.28 (2H, AA'BB', C$_6$H$_4$), 7.48 (2H, AA'BB', C$_6$H$_4$), 7.51 (2H, AA'BB', C$_6$H$_4$). $v_{max}$(KBr disc)/cm$^{-1}$: 2954 (CH$_3$—, C—H asym str), 2922 (—CH$_2$—, C—H asym str), 2854 (CH$_3$—, —CH$_2$—, C—H sym str), 1605, 1521 and 1480 (C═C str), 1463 (CH$_3$— asym, —CH$_2$— sci, C—H def), 1401, 1250 (Si—C and aryl-O str), 1054 (Si—O—Si, Si—O—C asym str and C—O str), 840 and 804 (Si—CH$_3$, Si—O—C def and C—H o.o.p.d.). m/z: 610 [M]$^+$, 609, 539, 497, 408, 295.

EXAMPLE 20

2-[2,3-Difluoro-4-(4pentamethyldisiloxybutyloxy) biphenyl-4'-yl]-5-nonyl-1,3-dioxane (Compound No 21 in Table 3)

Quantities: pentamethyldisiloxane (0.22 g, 1.5mmol) and 2-[4-(3-butenyloxy)-2,3-difluorobiphenyl-4'-yl]-5-nonyl-1,3-dioxane (Preparation 21, 0.5 g, 1 mmol). The experimental procedure was described previously in Example 14.

Yield=0.4 g (64%); Purity (HPLC): 100.0%; Element Analysis: Calc. (found) for $C_{36}H_{52}F_2O_2Si_2$ (610.97): C, 65.76 (66.34); H, 8.77 (9.12) %. Mesomorphism (T/° C.): Cryst 47 $S_B$ 51.4 $S_C$ 87.5 $S_A$ 103.0 Iso.

$\delta_H$ (270 MHz; CDCl$_3$; Me$_4$Si): 0.07 (15H, m, 5×SiCH$_3$), 0.58 (2H, t, J 8.4, SiCH$_2$), 0.89 (3H, t, J 6.6, CH$_3$), 1.11 (2H, m, CH$_2$CH$_3$), 1.28 (14H, m, C$_7$H$_4$), 1.53 (2H, m, OCH$_2$CH$_2$CH$_2$), 1.86 (2H, qn, J 7.0, OCH$_2$CH$_2$), 2.14 (1H, m, 5-H), 3.55 (2H, dd, J 11.5 and 11.5, Ha), 4.08 (2H, t, J 6.5, OCH$_2$), 4.25 (2H, dd, J 11.5 and 4.5, He), 5.45 (1H, s, 2-H), 6.79 (1H, ABXY, OC$_6$H$_2$F$_2$), 7.07 (1H, ABXY, C$_6$F$_2$H$_2$), 7.50 (2H, AA'BB', C$_6$H$_4$), 7.55 (2H, AA'BB', C$_6$H$_4$). $v_{max}$(film)/cm$^{-1}$: 2950 (CH$_3$—, C—H asym str), 2920 (—CH$_2$—, C—H asym str), 2848 (CH$_3$—, —CH$_2$—, C—H sym str), 1630 and 1499 (C═C str), 1465 (CH$_3$— asym, —CH$_2$— sci, C—H def), 1391, 1251 (Si—C and aryl-O str), 1078 (Si—O—Si, Si—O—C asym str and C—O str), 842 and 800 (Si—CH$_3$, Si—O—C def and C—H o.o.p.d.). m/z: 563 [M-57, —C$_4$H$_9$]$^+$, 549, 464.

EXAMPLE 21

2,3-Difluoro-4-(5,5,6,6,7,7,8,8,8-nonafluoroocty-loxy)-4'-(4-pentamethyldisiloxybutyloxy)biphenyl (Compound 16 in Table 2)

Quantities: pentamethyldisiloxane (0.18 g, 1.2 mmol) and 4'-(3-butenyloxy)-2,3-difluoro-4-(5,5,6,6,7,7,8,8,8-nonafluorooctyloxy)biphenyl (Preparation 22, 0.45 g, 0.8 mmol). The experimental procedure was described in Example 14.

Yield=0.25 g (45%); mp. 48-49° C.; Purity (HPLC): 100.0%; Element Analysis: Calc. (found) for $C_{29}H_{37}F_{11}O_3Si_2$ (698.76): C, 49.85 (49.99); H, 5.34 (5.34) %.

$\delta_H$ (270 MHz; CDCl$_3$): 0.07 (15H, m, 5×SiCH$_3$), 0.59 (2H, t, J 8.3, SiCH$_2$), 1.50 (2H, m, SiCH$_2$CH$_2$), 1.89 (6H, m, OCH$_2$CH$_2$, C$_2$H$_4$), 2.20 (2H, m, CF$_2$CH$_2$), 4.01 (2H, t, J 6.5, OCH$_2$Rf), 4.12 (2H, t, J 5.7, OCH$_2$), 6.77 (1H, ABXY, OC$_6$F$_2$H$_2$), 6.97 (2H, AA'BB', OC$_6$H$_4$), 7.07 (1H, ABXY, C$_6$F$_2$H$_2$), 7.42 (2H, AA'BB', C$_6$H$_4$). $v_{max}$(KBr disc)/cm$^{-1}$: 2956 (—CH$_2$—, C—H asym str), 2886 (—CH$_2$—, C—H sym str), 1625, 1603 and 1500 (C═C str), 1463 (—CH$_2$— sci, C—H det), 1252, 1222 and 1217 (Si—C, C—F and aryl-O str), 1129 and 1078 (Si—O—Si, Si—O—C asym str and C—O str), 839 (Si—CH$_3$, Si—O—C def and C—H o.o.p.d.). m/z: 698 [M]$^+$, 680, 663.

EXAMPLE 22

2,3-Difluoro-4'-(5,5,6,6,7,7,8,8,8-nonafluoroocty-loxy)-4-(4-pentamethyldisiloxybutyloxy)biphenyl (Compound 17 in Table 2)

Quantities: pentamethyldisiloxane (0.12 g, 0.82 mmol) and 4-(3-butenyloxy)-2,3-difluoro-4'-(5,5,6,6,7,7,8,8,8-nonafluorooctyloxy)biphenyl (Preparation 23, 0.3 g, 0.55 mmol). The experimental procedure was described previously in Example 14.

Yield=0.2 g (52%); mp. 40-42° C.; Purity (HPLC): 100.0%; Element Analysis: Calc. (found) for $C_{29}H_{37}F_{11}O_3Si_2$ (698.76): C, 49.85 (49.89); H, 5.34 (5.23) %.

$\delta_H$ (270 MHz; $CD_2Cl_2$; ExRef 5.30): 0.06 (1H, m, 5×SiCH$_3$), 0.58 (2H, t, J 8.3, SiCH$_2$), 1.50 (2H, m, SiCH$_2$CH$_2$), 1.85 (6H, m, OCH$_2$CH$_2$, C$_2$H$_4$), 2.18 (2H, m, CF$_2$CH$_2$), 4.02 (2H, t, J 6.0, OCH$_2$Rf), 4.06 (2H, t, J 6.5, OCH$_2$), 6.80 (1H, ABXY, OC$_6$F$_2$H$_2$), 6.94 (2H, AA'BB', OC$_6$H$_4$), 7.07 (1H, ABXY, C$_6$F$_2$H$_2$), 7.41 (2H, AA'BB', $C_6H_4$). $\nu_{max}$(KBr disc)/cm$^{-1}$: 2954 (—CH$_2$—, C—H asym str), 2874 (—CH$_2$—, C—H sym str), 1626, 1607 and 1501 (C=C str), 1465 (—CH$_2$— sci, C—H det), 1249 and 1232 (Si—C, C—F and aryl-O str), 1132 and 1074 (Si—O—Si, Si—O—C asym str and C—O str), 843 and 806 (Si—CH$_3$, Si—O—C def and C—H o.o.p.d.). m/z: 698 [M]$^+$, 685, 642, 626, 551, 531, 496.

EXAMPLE 23

1.7-Di{4-[2,3-difluoro-4'-(5,5,5,6,6,7,7,8,8,8-nonafluorooctyloxy)biphenyl-4-oxy]butyl}-octamethyltetrasiloxane (Dimer of Compound 17 in Table 2)

Quantities: 1,1,3,3,5,5,7,7-octamethyltetrasiloxane (86.9 mg, 0.31 mmol) and 4-(3-butenyloxy)-2,3-difluoro-4'-(5,5,6,6,7,7,8,8,8-nonafluorooctyloxy)biphenyl (Example 22, 0.35 g, 0.64 mmol). The experimental procedure was described previously in Example 14 without recrystallisation.

Yield=0.2 g (47%); Purity (HPLC): 100.0%; Element Analysis: Calc. (found) for $C_{56}H_{68}F_{22}O_7Si_4$ (1383.46): C, 48.62 (47.93); H, 4.95 (4.94)%. Mesomorphism (T/° C.): Cryst 5.21 (DSC, onset) $S_C$ 12.5 $S_A$ 34.6 Iso.

$\delta_H$ (270 MHz; CDCl$_3$; ExRef 7.26): 0.07 (24H, m, 8×SiCH$_3$), 0.61 (4H, t, J 8.5, 2×SiCH$_2$), 1.54 (4H, m, SiCH$_2$CH$_2$), 1.87 (12H, m, 2×OCH$_2$CH$_2$, 2×C$_2$H$_4$), 2.17 (4H, m, 2×CF$_2$CH$_2$), 4.03 (4H t, J 5.8, 2×OCH$_2$Rf), 4.06 (4H, t, J 6.5, 2×OCH$_2$), 6.77 (2H, ABXY, OC$_6$F$_2$H$_2$), 6.94 (4H, AA'BB', OC$_6$H$_4$), 7.04 (2H, ABXY, C$_6$F$_2$H$_2$), 7.42 (4H, AA'BB', C$_6$H$_4$). $\nu_{max}$(KBr disc)/cm$^{-1}$: 2956 (—CH$_2$—, C—H asym str), 2876 (—CH$_2$—, C—H sym str), 1624, 1605 and 1495 (C=C str), 1466 (—CH$_2$— sci, C—H def), 1254 and 1232 (Si—C, C—F and aryl-O str), 1130, 1076 and 1036 (Si—O—Si, Si—O—C asym str and C—O str), 836 and 797 (Si—CH$_3$, Si—O—C def and C—H o.o.p.d.).

EXAMPLE 24

Liquid Crystal Properties

Liquid crystal properties of the compounds of the invention and some comparative compounds were tested and the results are shown in following Tables 4-7

TABLE 4

Effect of Fluoro-substitution in Terminal end-chains of 3 ring systems

| Compound. No | Properties |
|---|---|
| Compound 1 in Table 1 | K 127 $S_c$ 183.8 $S_A$ 216.1° C. Iso |
| Comparative compound $H_{13}C_6O$—[C$_6$H$_2$F$_2$]—[C$_6$H$_4$]—[C$_6$H$_4$]—OC$_8$H$_{17}$ | K 117.5 $S_c$ 180.7 $S_A$ 181.5 N 216.1° C. Iso |
| Compound 2 in Table 1 | K 83 $S_c$ 155.7 $S_A$ 193.2° C. Iso |
| Comparative Compound $H_{13}C_6O$—[C$_6$H$_4$]—[C$_6$H$_2$F$_2$]—[C$_6$H$_4$]—OC$_8$H$_{17}$ | K 92 $S_c$ 128.4 $S_A$ 166.5° C. Iso |
| Compound 3 in Table 1 | K 99 $S_c$ 184.7 $S_A$ 206.8° C. Iso |
| Compound 4 in Table 1 | K 76 $S_c$ 116.4 $S_A$ 163.6° C. Iso |
| Compound 22 in Table 3 | K 78 $S_A$ 164.0° C. Iso |

The results in Table 4 illustrate that the compounds of the invention have a stabilised Smectic A phase as compared to structurally similar compounds. Thus these compounds may be particularly useful in mixtures to either induce or generate a smectic A phase where one is not present, or to provide for a wider temperature range smectic A phase for purposes of alignment or electroclinic devices. The results suggest that control of mesophase type, transition temperatures, and mesophase sequences may be achieved by making changes to the end-chain.

TABLE 5

Effect of Fluoro substitution in Terminal end chains of Two-ring systems

| Compound. No | Properties |
|---|---|
| Comparative compound $H_{17}C_8O$—[C$_6$H$_2$F$_2$]—[C$_6$H$_4$]—OC$_8$H$_{17}$ | K 57 $S_c$ 59.5 $S_A$ 60.1 N 63.7° C. Iso |

TABLE 5-continued

Effect of Fluoro substitution in Terminal end chains of Two-ring systems

| Compound. No | Properties |
|---|---|
| Compound 9 in Table 2 | K 47 $S_A$ 82.9° C. Iso (recryst~74° C.) |
| Compound 10 in Table 2 | K 74 $S_A$ 82.0° C. Iso (recryst~65° C.) |
| Compound 11 in Table 2 | K 83 $S_A$ 90.8° C. Iso (recryst~74° C.) |
| Compound 12 in Table 2 | K 47 $S_A$ 54.6° C. Iso (recryst~26° C.) |
| Compound 13 in Table 2 | K 50 $S_A$ 60.2° C. Iso (recryst~40° C.) |

These results show a similar trend with respect to the stabilisation of the Smectic A phase (at the expense of the Smectic C phase), albeit with higher melting points.

TABLE 6

Effect of Silioxy substitution in Terminal end chains of Three-ring systems

| Compound. No | Properties |
|---|---|
| Compound No 5 in Table 1 | K 53 $S_c$ 137.8° C. |
| Comparative compound (structure shown) | K 117.5 $S_c$ 180.7 $S_A$ 181.5 N 216.1° C. Iso |
| Compound 6 in Table 1 | K 70 $S_C$ 104.0 N 105.6° C. Iso |
| Comparative compound (structure shown) | K 92 $S_c$ 128.4 N 166.5° C. Iso |
| Compound 7 in Table 1 | K 54 $S_C$ 119.6° C. Iso |
| Compound 8 in Table 1 | K 28 $S_C$ 70.9 N 74.1° C. Iso |
| Compound 21 in Table 3 | K 47 $S_B$ 51.4. $S_C$ 87.5° C. $S_A$ 103° C. Iso |
| Dimer of Compound 17 in Table 2 (structure shown) | K 5.2 $S_{C(alt)}$ 12.5 $S_A$ 34.6° C. Iso |

Compounds of the invention which include silyl groups have lower clearing points when compared with the fluorinated compounds. The Smectic A phase now is totally depressed, and direct Smectic C to nematic or isotropic liquid transitions are observed. The silyl groups in this case are bulky but flexible due to the relative size of the silicon atoms and the linking oxygen.

Results with two ring systems suggest that silyl groups were not as good at supporting liquid crystal stability as the stiffer partially fluorinated end-groups, as some compounds were not mesogenic. However, when dimerised, the desirable properties of both end groups were retained (low melting point, an alternating shift smectic C phase (SmC (alt)—antiferroelectric-like ordering) due to the silyl group and a smectic A phase due to the fluoro-end chain.

TABLE 7

Fluoro-substituted end chain chiral Biphenyl Esters

| Compound. No | Properties |
|---|---|
| Compound No 18 in Table 2 | K 48 $S_A$* 53.2° C. Iso (recrys~22° C.) |
| Compound No 19 in Table 2 | K 65 ($S_A$* 60.2)° C. Iso (recrys~38° C.) |
| Compound No 20 in Table 2 | mp 43-45° C. |

The compounds in Table 7 had inherently low viscosities making them suitable for ferroelectric mixtures. Esters also show a propensity for exhibiting antiferroelectric phases. In addition, a strongly polar chiral groups with either chloro- or fluoro-substituents attached to a chiral carbon atom was positioned in the terminal aliphatic chain. This template was used in order to confer a strong coupling of the lateral dipoles in the system with the consequence that a large spontaneous polarization would be produced. Without these groups, chiral moieties with large lateral groups exhibited no liquid crystal behaviour but maybe useful as chiral dopants.

What is claimed is:

1. A liquid crystal compound of formula (I)

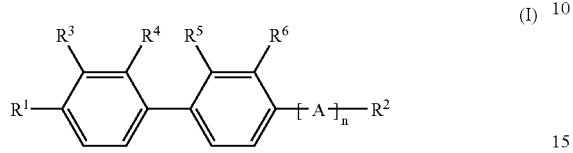

or a dimer thereof;

where $R^1$ and $R^2$ are independently selected from optionally substituted alkyl, and a functional group selected from halo, cyano, nitro, oxo, $C(O)R^a$, $OR^a$, $S(O)_tR^a$, $NR^bR^c$, $OC(O)NR^bR^c$, $C(O)NR^bR^c$, $OC(O)NR^bR^c$, $-NR^cC(O)_nR^b$, $-NR^aCONR^bR^c$, $-NR^aCSNR^bR^c$, $-C=NOR^a$, $-N=CR^bR^c$, $S(O)_tNR^bR^c$, or $-NR^bS(O)_tR^a$ where $R^a$, $R^b$ and $R^c$ are independently selected from hydrogen or optionally substituted hydrocarbyl, or $R^b$ and $R^c$ together form an optionally substituted ring which optionally contains further heteroatoms such as $S(O)_s$, oxygen and nitrogen, s is 0, 1 or 2, t is 0 or an integer of 1-3, or a group of sub-formula (i) provided that at least one of $R^1$ or $R^2$ is a group of sub-formula (i);

$$-(O)_m-(CH_2)_p-R^7 \qquad (i)$$

where m is 0 or 1;

p is an integer of from 3 to 12;

$R^7$ is a group of formula $-C_qX_{2q+1}$ where q is an integer of from 2 to 12 and X is halogen, or $R^7$ is a group of sub-formula (ii)

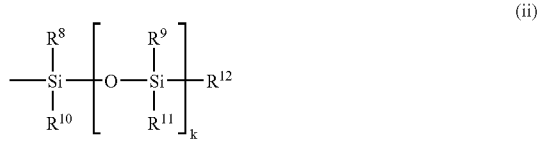

where k is an integer of from 1 to 10, $R^8$, $R^{10}$, and $R^{12}$ and each $R^9$ and $R^{11}$ are independently selected from alkyl, alkenyl or aryl;

$R^3$, $R^4$, $R^5$ and $R^6$ are independently selected from hydrogen or halogen, n is 0 or 1, and A is a group of sub-formula (iii), (iv), (v), (vi) or (vii)

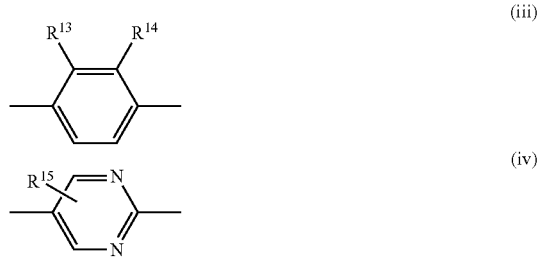

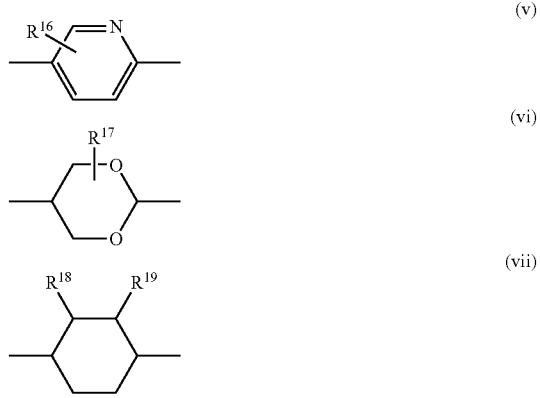

where $R^{13}$, $R^{14}$, $R^{15}$, $R^{16}$, $R^{17}$, $R^{18}$ and $R^{19}$ are independently selected from hydrogen or halo, and the group A may be orientated in either direction, so that the group $R^2$ is attached at either of the available bonds in sub-formula (iii)-(vii);

and further provided that where $R^2$ is a group of sub-formula (i), m=1, n=0, p=3 and $R^3$, $R^4$, $R^5$ and $R^6$ are each hydrogen and $R^7$ is a group of sub-formula (ii) in which k=1, $R^8$, $R^9$, $R^{10}$ and $R^{11}$ are each methyl and $R^{12}$ is a phenyl group, then $R^1$ shall not be either OMe or OBu; and further provided that at least one of the rings carries one or more halo atoms.

2. A compound according to claim 1 wherein the other of $R^1$ or $R^2$ is a functional group of formula $OR^a$, where $R^a$ is an alkyl group.

3. A compound according to claim 1 wherein both of the groups $R^1$ and $R^2$ are groups of sub-formula (i).

4. A compound according to claim 1 wherein in the group of sub-formula (i), m is 1.

5. A compound according to claim 1 wherein $R^7$ in the group of sub-formula (i) is a group of formula $-C_qX_{2q+1}$, q is as defined in claim 1 and each X is the same halogen.

6. A compound according to claim 5 wherein X is fluoro.

7. A compound according to claim 1 wherein $R^7$ is a group of sub-formula (ii).

8. A compound according to claim 7 wherein $R^8$, $R^9$, $R^{10}$, $R^{11}$ and $R^{12}$ are the same or different and are $C_{1-4}$alkyl groups.

9. A compound according to claim 7 wherein the integer k is 1.

10. A compound according to claim 1 wherein n is 1.

11. A compound according to claim 1 where A is a group of sub-formula (iii) as defined in claim 1.

12. A compound according to claim 1 wherein n is 0, and at least one group $R^1$ or $R^2$ is a group of sub-formula (i) where $R^7$ is a group of formula $-C_qX_{2q+1}$, wherein q is as defined in claim 1.

13. A compound according to claim 1 wherein $R^3$ and $R^4$ or $R^5$ and $R^6$, or when ring A is present $R^{13}$ and $R^{14}$, or $R^{18}$ and $R^{19}$ are fluoro atoms.

14. A method for preparing a compound according to claim 1 which method comprises coupling a compound of formula (IV)

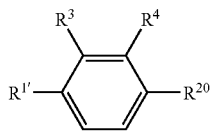
(IV)

where R³ and R⁴ are as defined in claim 1 and R¹' is a group R¹ as defined in claim 1 or a precursor thereof, and R²⁰ is a reactive group, suitable for a coupling reaction, with a compound of formula (V)

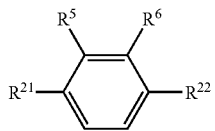
(V)

where R⁵ and R⁶ are as defined in claim 1, R²² is a group $(A)_n$-R²' where A and n are as defined in claim 1 and R²' is a group as defined in claim 1 or a precursor thereof, and R²¹ is a leaving group, suitable for a coupling reaction; and thereafter if necessary converting a precursor group R¹' or R²' to a group R¹ or R² respectively.

15. A method for preparing a compound according to claim 1 wherein n is 1, said method comprising reacting a compound of formula (VI)

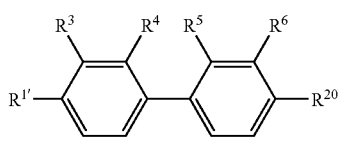
(VI)

where R³, R⁴, R⁵ and R⁶ are as defined in claim 1, and R¹' is a group R¹ as defined in claim 1 or a precursor thereof, and R²⁰ is a reactive group, suitable for a coupling reaction with a compound of formula (VII)

R²²-A-R²'  (VII)

where A is as defined in claim 1 and R²² is a group $(A)_n$-R²' where A and n are as defined in claim 1 and R²' is a group as defined in claim 1, or a precursor thereof, and thereafter if necessary converting a precursor group R¹' or R²' to a group R¹ or R² respectively.

16. A liquid crystal device comprising a compound according to claim 1.

17. A device according to claim 16 wherein the compound of formula (I) has liquid crystal properties.

18. A first liquid crystal mixture comprising a compound according to claim 1.

19. A method of stabilizing a smectic A phase in a liquid crystal mixture comprising the step of adding a compound according to claim 1 to the liquid crystal mixture.

20. A method of stabilizing a smectic A phase in a second liquid crystal mixture comprising the step of adding a first liquid crystal mixture according to claim 18 to the said second liquid crystal mixture.

21. A compound according to claim 1 wherein R³, R⁴, R⁵ and R⁶ are fluorine.

22. A compound according to claim 1, wherein when R⁷ is —$C_qX_{2q+1}$ then the other terminal end chain is not chiral.

23. A method of stabilizing a smectic A phase in a liquid crystal mixture comprising the step of adding a liquid crystal compound of formula (I), to the liquid crystal mixture,

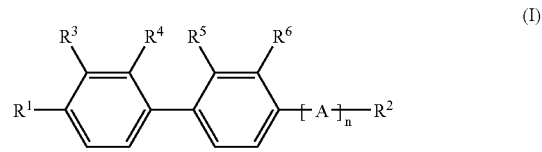
(I)

or a dimer thereof;

where R¹ and R² are independently selected from optionally substituted alkyl, optionally substituted alkenyl, optionally substituted alkynyl, a functional group selected from halo, cyano, nitro, oxo, $C(O)_n$'Rᵃ, ORᵃ, $S(O)_t$Rᵃ, NRᵇRᶜ, OC(O)NRᵇRᶜ, C(O)NRᵇRᶜ, OC(O)NRᵇRᶜ, —NRᶜC(O)$_n$'Rᵇ, —NRᵇCONRᵇRᶜ, —NRᵃCS-NRᵇRᶜ, —C=NORᵃ, —N=CRᵇRᶜ, S(O)$_t$NRᵇRᶜ, or —NR S(O)$_t$Rᵃ where Rᵃ, Rᵇ and Rᶜ are independently selected from hydrogen or optionally substituted hydrocarbyl, or Rᵇ and Rᶜ together form an optionally substituted ring which optionally contains further heteroatoms such as $S(O)_s$, oxygen and nitrogen, n' is 1 or 2, s is 0, 1 or 2, t is 0 or an integer of 1-3, or a group of sub-formula (i) provided that at least one of R¹ or R² is a group of sub-formula (i);

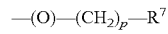
—(O)—(CH₂)$_p$—R⁷  (i)

where m is 0 or 1;

p is an integer of from 3 to 12;

R⁷ is a group of formula —$C_qX_{2q+1}$ where q is an integer of from 2 to 12 and X is halogen, or R⁷ is a group of sub-formula (ii)

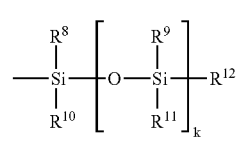
(ii)

where k is an integer of from 1 to 10, R⁸, R¹⁰ and R¹² and each R⁹ and R¹¹ are independently selected from alkyl, alkenyl or aryl;

R³, R⁴, R⁵ and R⁶ are independently selected from hydrogen or halogen, n is 0 or 1, and A is a group of sub-formula (iii), (iv), (v), (vi) or (vii)

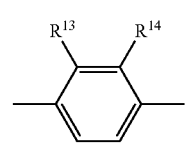
(iii)

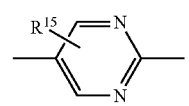
(iv)

-continued

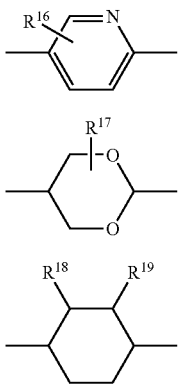

(v)

(vi)

(vii)

where $R^{13}$, $R^{14}$, $R^{15}$, $R^{16}$, $R^{17}$, $R^{18}$ and $R^{19}$ are independently selected from hydrogen or halo, and the group A may be orientated in either direction, so that the group $R^2$ is attached at either of the available bonds in sub-formula (iii)-(vii);

and further provided that where $R^2$ is a group of sub-formula (i), m=1, n=0, p=3 and $R^3$, $R^4$, $R^5$ and $R^6$ are each hydrogen and $R^7$ is a group of sub-formula (ii) in which k=1, $R^8$, $R^9$, $R^{10}$ and $R^{11}$ are each methyl and $R^{12}$ is a phenyl group, then $R^1$ shall not be either OMe or OBu; and further provided that at least one of the rings carries one or more halo atoms.

24. A liquid crystal compound of formula (I)

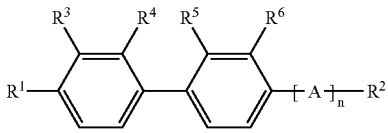

(I)

or a dimer thereof;

where $R^1$ and $R^2$ are independently selected from optionally substituted alkyl, optionally substituted alkenyl, optionally substituted alkynyl, a functional group selected from halo, cyano, nitro, oxo, C(O)$R^a$, O$R^a$, S(O)$_t R^a$, N$R^b R^c$, OC(O)N$R^b R^c$, C(O)N$R^b R^c$, OC(O)N$R^b R^c$, —N$R^c$C(O)$_n$'$R^b$, —N$R^a$CON$R^b R^c$, —N$R^a$CS-N$R^b R^c$, —C=NO$R^a$, —N=C$R^b R^c$, S(O)$_t$N$R^b R^c$, or —N$R^b$S(O)$_t R^a$ where $R^a$, $R^b$ and $R^c$ are independently selected from hydrogen or optionally substituted hydrocarbyl, or $R^b$ and $R^c$ together form an optionally substituted ring which optionally contains further heteroatoms such as S(O)$_s$, oxygen and nitrogen, s is 0, 1 or 2, t is 0 or an integer of 1-3, or a group of sub-formula (i) provided that at least one of $R^1$ or $R^2$ is a group of sub-formula (i);

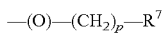

(i)

where m is 0 or 1;

p is an integer of from 3 to 12;

$R^7$ is a group of sub-formula (ii)

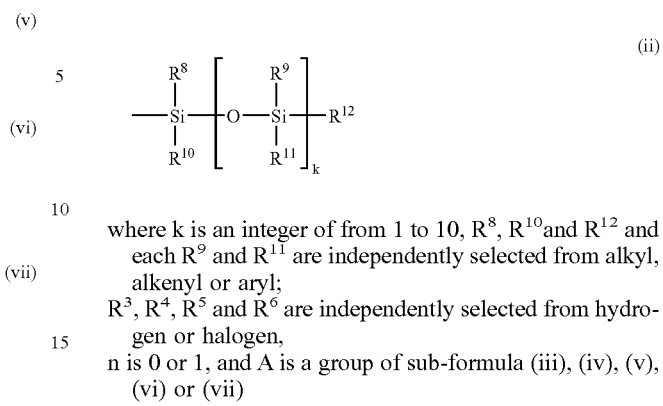

(ii)

where k is an integer of from 1 to 10, $R^8$, $R^{10}$ and $R^{12}$ and each $R^9$ and $R^{11}$ are independently selected from alkyl, alkenyl or aryl;

$R^3$, $R^4$, $R^5$ and $R^6$ are independently selected from hydrogen or halogen, n is 0 or 1, and A is a group of sub-formula (iii), (iv), (v), (vi) or (vii)

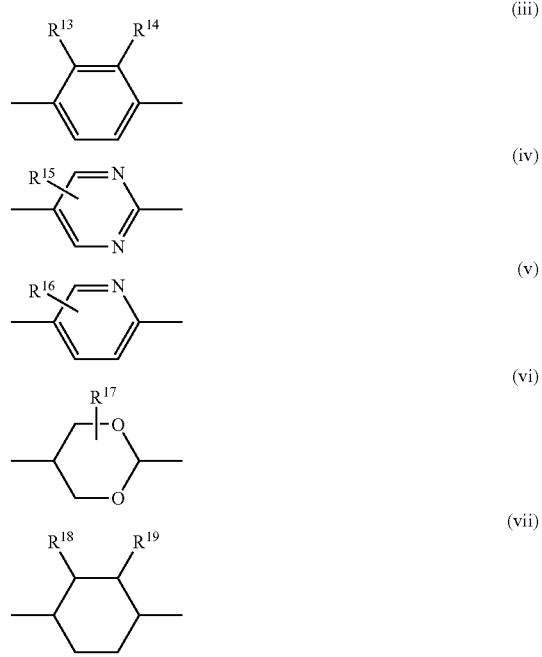

(iii)

(iv)

(v)

(vi)

(vii)

where $R^{13}$, $R^{14}$, $R^{15}$, $R^{16}$, $R^{17}$, $R^{18}$ and $R^{19}$ are independently selected from hydrogen or halo, and the group A may be orientated in either direction, so that the group $R^2$ is attached at either of the available bonds in sub-formula (iii)-(vii);

and further provided that where $R^2$ is a group of sub-formula (i), m =1, n =0, p =3 and $R^3$, $R^4$, $R^5$ and $R^6$ are each hydrogen and $R^7$ is a group of sub-formula (ii) in which k=1, $R^8$, $R^9$, $R^{10}$ and $R^{11}$ are each methyl and $R^{12}$ is a phenyl group, then $R^1$ shall not be either OMe or OBu; and further provided that at least one of the rings carries one or more halo atoms.

25. A compound according to claim 24 wherein $R^8$, $R^9$, $R^{10}$, $R^{11}$ and $R^{12}$ are the same or different and are $C_{1-4}$ alkyl groups.

26. A compound according to claim 24 wherein the integer k is 1.

* * * * *